US009603752B2

(12) United States Patent
Brown et al.

(10) Patent No.: US 9,603,752 B2
(45) Date of Patent: Mar. 28, 2017

(54) APPARATUS AND METHOD FOR MINIMIZING WASTE AND IMPROVING QUALITY AND PRODUCTION IN WEB PROCESSING OPERATIONS BY AUTOMATIC CUFF DEFECT CORRECTION

(75) Inventors: Jeffrey D Brown, Sheboygan, WI (US); Dennis J Faucher, Sheboygan, WI (US); Jeffrey W Fritz, Plymouth, WI (US); Gottfried J Hohm, Sheboygan Falls, WI (US); Adam D DeNoble, De Pere, WI (US); Ryan M Ferguson, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 617 days.

(21) Appl. No.: 13/196,663

(22) Filed: Aug. 2, 2011

(65) Prior Publication Data
US 2012/0202664 A1    Aug. 9, 2012

Related U.S. Application Data

(60) Provisional application No. 61/400,969, filed on Aug. 5, 2010.

(51) Int. Cl.
*A61F 13/15*    (2006.01)
*B65H 23/032*    (2006.01)

(52) U.S. Cl.
CPC .. *A61F 13/15772* (2013.01); *A61F 13/15804* (2013.01); *B65H 23/032* (2013.01); *A61F 2013/15796* (2013.01)

(58) Field of Classification Search
CPC ...... B65H 23/00; B65H 23/04; B65H 23/046; B65H 23/048; B65H 45/00; B65H 45/12;
(Continued)

(56) References Cited

U.S. PATENT DOCUMENTS 135,145 A    1/1873    Murphy
293,353 A    2/1884    Purvis
(Continued)

FOREIGN PATENT DOCUMENTS

BE    1007854    11/1995
CA    1146129    5/1983
(Continued)

OTHER PUBLICATIONS

International Search Report dated Nov. 3, 2011 regarding EP Application No. 11250672.0, 4 pages.
(Continued)

*Primary Examiner* — Christopher Harmon
(74) *Attorney, Agent, or Firm* — Ryan Kromholz & Manion, S.C.

(57) ABSTRACT

Apparatus and methods are provided to minimize waste and improve quality and production in web processing operations. The apparatus and methods provide defect detection both before and after application of component patches to a traveling web to create a product. Web defect detection may be provided by way of at least one visual inspection station located upstream from the patch applicator. Patch defect detection may be accomplished by way of a visual inspection station located proximate the patch applicator. If defects are detected in either the traveling web or the component patch prior to patch application, patch application may be prevented until both a satisfactory web and patch are provided. If defects are detected after patch application, the resulting product may be culled. Furthermore, the apparatus may be provided with diagnostic software to warn against extant or imminent machine complications.

3 Claims, 12 Drawing Sheets

(58) Field of Classification Search
CPC  B65H 2301/32; B65H 2301/331; B31B 1/36; B31B 3/02; B31B 3/26; B31B 2201/2637
USPC ............. 493/405, 416, 417, 436, 439, 8, 12
See application file for complete search history.

(56) References Cited

U.S. PATENT DOCUMENTS

| | | |
|---|---|---|
| 312,257 A | 2/1885 | Cotton et al. |
| 410,123 A | 8/1889 | Stilwell |
| 432,742 A | 7/1890 | Stanley |
| 643,821 A | 2/1900 | Howlett |
| 1,393,524 A | 10/1921 | Grupe |
| 1,431,315 A | 10/1922 | Le Moine |
| 1,605,842 A | 11/1926 | Jones |
| 1,629,681 A | 5/1927 | Cram |
| 1,686,595 A | 10/1928 | Belluche |
| 1,957,651 A | 5/1934 | Joa |
| 2,009,857 A | 7/1935 | Potdevin |
| 2,054,832 A | 9/1936 | Potdevin |
| 2,117,432 A | 5/1938 | Linscott |
| 2,128,746 A | 8/1938 | Joa |
| 2,131,808 A | 10/1938 | Joa |
| 2,164,408 A | 7/1939 | Joa |
| 2,167,179 A | 7/1939 | Joa |
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,627,859 A | 2/1953 | Hargrave |
| 2,695,025 A | 11/1954 | Andrews |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,788,786 A | 4/1957 | Dexter |
| 2,811,905 A | 11/1957 | Kennedy, Jr. |
| 2,828,745 A | 4/1958 | Deutz |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,890,700 A | 6/1959 | Lonberg-Holm |
| 2,913,862 A | 11/1959 | Sabee |
| 2,939,461 A | 6/1960 | Joa |
| 2,939,646 A | 6/1960 | Stone |
| 2,960,143 A | 11/1960 | Joa |
| 2,990,081 A | 6/1961 | De Neui et al. |
| 2,991,739 A | 7/1961 | Joa |
| 3,016,207 A | 1/1962 | Comstock, III |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et al. |
| 3,086,253 A | 4/1963 | Joa |
| 3,087,689 A | 4/1963 | Heim |
| 3,089,494 A | 5/1963 | Schwartz |
| 3,091,408 A | 5/1963 | Schoeneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,318,608 A | 5/1967 | Smrekar |
| 3,322,589 A | 5/1967 | Joa |
| 3,342,184 A | 9/1967 | Joa |
| 3,356,092 A | 12/1967 | Joa |
| 3,360,103 A | 12/1967 | Joa |
| 3,363,847 A | 1/1968 | Joa |
| 3,391,777 A | 7/1968 | Joa |
| 3,454,442 A | 7/1969 | Heller, Jr. |
| 3,463,413 A | 8/1969 | Smith |
| 3,470,848 A | 10/1969 | Dreher |
| 3,484,275 A | 12/1969 | Lewicki, Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo |
| 3,575,170 A | 4/1971 | Clark |
| 3,607,578 A | 9/1971 | Berg et al. |
| 3,635,462 A | 1/1972 | Joa |
| 3,656,741 A | 4/1972 | Macke et al. |
| 3,666,611 A | 5/1972 | Joa |
| 3,673,021 A | 6/1972 | Joa |
| 3,685,818 A | 8/1972 | Burger et al. |
| 3,728,191 A | 4/1973 | Wierzba et al. |
| 3,751,224 A | 8/1973 | Wackerle |
| 3,758,102 A | 9/1973 | Munn et al. |
| 3,772,120 A | 11/1973 | Radzins |
| 3,776,798 A | 12/1973 | Milano |
| 3,796,360 A | 3/1974 | Alexeff |
| 3,811,987 A | 5/1974 | Wilkinson et al. |
| 3,816,210 A | 6/1974 | Aoko et al. |
| 3,847,710 A | 11/1974 | Blomqvist et al. |
| 3,854,917 A | 12/1974 | McKinney et al. |
| 3,883,389 A | 5/1975 | Schott, Jr. |
| 3,888,400 A | 6/1975 | Wiig |
| 3,901,238 A | 8/1975 | Gellert et al. |
| 3,903,768 A | 9/1975 | Amberg et al. |
| 3,904,147 A | 9/1975 | Taitel et al. |
| 3,918,968 A | 11/1975 | Coast |
| 3,960,646 A | 6/1976 | Wiedamann |
| 3,988,194 A | 10/1976 | Babcock et al. |
| 3,991,994 A | 11/1976 | Farish |
| 4,002,005 A | 1/1977 | Mueller et al. |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |

(56) References Cited

U.S. PATENT DOCUMENTS

| | | | |
|---|---|---|---|
| 4,231,129 A | 11/1980 | Winch | |
| 4,236,955 A | 12/1980 | Prittie | |
| 4,275,510 A | 6/1981 | George | |
| 4,284,454 A | 8/1981 | Joa | |
| 4,307,800 A | 12/1981 | Joa | |
| 4,316,756 A | 2/1982 | Wilson | |
| 4,325,519 A | 4/1982 | McLean | |
| 4,342,206 A | 8/1982 | Rommel | |
| 4,364,787 A | 12/1982 | Radzins | |
| 4,374,576 A | 2/1983 | Ryan | |
| 4,379,008 A | 4/1983 | Gross et al. | |
| 4,394,898 A | 7/1983 | Campbell | |
| 4,411,721 A | 10/1983 | Wishart | |
| 4,452,597 A | 6/1984 | Achelpohl | |
| 4,492,608 A | 1/1985 | Hirsch et al. | |
| 4,501,098 A | 2/1985 | Gregory | |
| 4,508,528 A | 4/1985 | Hirsch et al. | |
| 4,522,853 A | 6/1985 | Szonn et al. | |
| 4,543,152 A | 9/1985 | Nozaka | |
| 4,551,191 A | 11/1985 | Kock et al. | |
| 4,578,052 A * | 3/1986 | Engel et al. | 493/11 |
| 4,586,199 A | 5/1986 | Birring | |
| 4,589,945 A | 5/1986 | Polit | |
| 4,603,800 A | 8/1986 | Focke et al. | |
| 4,608,115 A | 8/1986 | Schroth et al. | |
| 4,610,097 A | 9/1986 | Kotitschke et al. | |
| 4,610,681 A | 9/1986 | Strohbeen et al. | |
| 4,610,682 A | 9/1986 | Kopp | |
| 4,614,076 A | 9/1986 | Rathemacher | |
| 4,619,357 A | 10/1986 | Radzins et al. | |
| 4,634,482 A | 1/1987 | Lammers | |
| 4,641,381 A | 2/1987 | Heran et al. | |
| 4,642,150 A | 2/1987 | Stemmler | |
| 4,642,839 A | 2/1987 | Urban | |
| 4,650,406 A * | 3/1987 | Peters | B29C 53/10 264/40.5 |
| 4,650,530 A | 3/1987 | Mahoney et al. | |
| 4,663,220 A | 5/1987 | Wisneski et al. | |
| 4,672,705 A | 6/1987 | Bors et al. | |
| 4,675,016 A | 6/1987 | Meuli et al. | |
| 4,675,062 A | 6/1987 | Instance | |
| 4,675,068 A | 6/1987 | Lundmark | |
| 4,686,136 A | 8/1987 | Homonoff et al. | |
| 4,693,056 A | 9/1987 | Raszewski | |
| 4,699,606 A * | 10/1987 | Whitley et al. | 493/4 |
| 4,701,239 A | 10/1987 | Craig | |
| 4,720,415 A | 1/1988 | Vander Wielen et al. | |
| 4,723,698 A | 2/1988 | Schoonderbeek | |
| 4,726,874 A | 2/1988 | Van Vliet | |
| 4,726,876 A | 2/1988 | Tomsovic, Jr. | |
| 4,743,241 A | 5/1988 | Igaue et al. | |
| 4,751,997 A | 6/1988 | Hirsch | |
| 4,753,429 A | 6/1988 | Irvine et al. | |
| 4,756,141 A | 7/1988 | Hirsch et al. | |
| 4,763,822 A | 8/1988 | Mohrsen | |
| 4,764,325 A | 8/1988 | Angstadt | |
| 4,765,780 A | 8/1988 | Angstadt | |
| 4,776,920 A | 10/1988 | Ryan | |
| 4,777,513 A | 10/1988 | Nelson | |
| 4,782,647 A | 11/1988 | Williams et al. | |
| 4,785,986 A | 11/1988 | Daane et al. | |
| 4,795,416 A * | 1/1989 | Cogswell et al. | 493/423 |
| 4,795,451 A | 1/1989 | Buckley | |
| 4,795,510 A | 1/1989 | Wittrock et al. | |
| 4,798,353 A | 1/1989 | Peugh | |
| 4,801,345 A | 1/1989 | Dussaud et al. | |
| 4,802,570 A | 2/1989 | Hirsch et al. | |
| 4,840,609 A | 6/1989 | Jones et al. | |
| 4,845,964 A | 7/1989 | Bors et al. | |
| 4,864,802 A | 9/1989 | D'Angelo | |
| 4,880,102 A | 11/1989 | Indrebo | |
| 4,888,231 A | 12/1989 | Angstadt | |
| 4,892,536 A | 1/1990 | Des Marais et al. | |
| 4,904,440 A | 2/1990 | Angstadt | |
| 4,908,175 A | 3/1990 | Angstadt | |
| 4,909,019 A | 3/1990 | Delacretaz et al. | |
| 4,915,767 A | 4/1990 | Rajala et al. | |
| 4,917,746 A | 4/1990 | Kons | |
| 4,925,520 A | 5/1990 | Beaudoin et al. | |
| 4,927,322 A | 5/1990 | Schweizer et al. | |
| 4,927,486 A | 5/1990 | Fattal et al. | |
| 4,927,582 A | 5/1990 | Bryson | |
| 4,937,887 A | 7/1990 | Schreiner | |
| 4,963,072 A | 10/1990 | Miley et al. | |
| 4,987,940 A | 1/1991 | Straub et al. | |
| 4,994,010 A | 2/1991 | Doderer-Winkler | |
| 5,000,806 A | 3/1991 | Merkatoris et al. | |
| 5,021,111 A | 6/1991 | Swenson | |
| 5,025,910 A | 6/1991 | Lasure et al. | |
| 5,045,039 A | 9/1991 | Bay | |
| 5,062,597 A | 11/1991 | Martin et al. | |
| 5,064,179 A | 11/1991 | Martin | |
| 5,064,492 A | 11/1991 | Friesch | |
| 5,080,741 A | 1/1992 | Nomura et al. | |
| 5,094,658 A | 3/1992 | Smithe et al. | |
| 5,096,532 A | 3/1992 | Neuwirth et al. | |
| 5,108,017 A | 4/1992 | Adamski, Jr. et al. | |
| 5,109,767 A | 5/1992 | Nyfeler et al. | |
| 5,110,403 A | 5/1992 | Ehlert | |
| 5,114,392 A * | 5/1992 | McAdam et al. | 493/179 |
| 5,127,981 A | 7/1992 | Straub et al. | |
| 5,131,525 A | 7/1992 | Musschoot | |
| 5,131,901 A | 7/1992 | Moll | |
| 5,133,511 A | 7/1992 | Mack | |
| 5,137,505 A * | 8/1992 | Ishii et al. | 493/248 |
| 5,147,487 A | 9/1992 | Nomura et al. | |
| 5,163,594 A | 11/1992 | Meyer | |
| 5,171,239 A | 12/1992 | Igaue et al. | |
| 5,176,244 A | 1/1993 | Radzins et al. | |
| 5,178,601 A * | 1/1993 | Lovenbrant | 493/423 |
| 5,183,252 A | 2/1993 | Wolber et al. | |
| 5,188,627 A | 2/1993 | Igaue et al. | |
| 5,190,234 A | 3/1993 | Ezekiel | |
| 5,195,684 A | 3/1993 | Radzins | |
| 5,203,043 A | 4/1993 | Riedel | |
| 5,212,656 A * | 5/1993 | Clary | B31B 1/74 493/12 |
| 5,213,645 A | 5/1993 | Nomura et al. | |
| 5,222,422 A | 6/1993 | Benner, Jr. et al. | |
| 5,223,069 A | 6/1993 | Tokuno et al. | |
| 5,226,992 A | 7/1993 | Morman | |
| 5,246,433 A | 9/1993 | Hasse et al. | |
| 5,252,228 A | 10/1993 | Stokes | |
| 5,267,933 A | 12/1993 | Precoma | |
| 5,273,228 A | 12/1993 | Yoshida | |
| 5,275,676 A | 1/1994 | Rooyakkers et al. | |
| 5,308,345 A | 5/1994 | Herrin | |
| 5,328,438 A | 7/1994 | Crowley | |
| 5,340,424 A | 8/1994 | Matsushita | |
| 5,368,893 A | 11/1994 | Sommer et al. | |
| 5,389,173 A | 2/1995 | Merkotoris et al. | |
| 5,393,360 A | 2/1995 | Bridges et al. | |
| 5,407,507 A | 4/1995 | Ball | |
| 5,407,513 A | 4/1995 | Hayden et al. | |
| 5,415,649 A | 5/1995 | Watanabe et al. | |
| 5,421,924 A | 6/1995 | Ziegelhoffer et al. | |
| 5,424,025 A | 6/1995 | Hanschen et al. | |
| 5,429,576 A | 7/1995 | Doderer-Winkler | |
| 5,435,802 A | 7/1995 | Kober | |
| 5,443,437 A * | 8/1995 | Mack | 493/359 |
| 5,449,353 A | 9/1995 | Watanabe et al. | |
| 5,464,401 A | 11/1995 | Hasse et al. | |
| 5,486,253 A | 1/1996 | Otruba | |
| 5,494,622 A | 2/1996 | Heath et al. | |
| 5,500,075 A | 3/1996 | Herrmann | |
| 5,516,392 A | 5/1996 | Bridges et al. | |
| 5,518,566 A | 5/1996 | Bridges et al. | |
| 5,525,175 A | 6/1996 | Blenke et al. | |
| 5,531,850 A | 7/1996 | Hermann | |
| 5,540,647 A | 7/1996 | Weiermann et al. | |
| 5,545,275 A | 8/1996 | Herrin et al. | |
| 5,545,285 A | 8/1996 | Johnson | |
| 5,552,013 A | 9/1996 | Ehlert et al. | |
| 5,556,360 A | 9/1996 | Kober et al. | |

(56) References Cited

U.S. PATENT DOCUMENTS

| | | |
|---|---|---|
| 5,556,504 A | 9/1996 | Rajala et al. |
| 5,560,793 A | 10/1996 | Ruscher et al. |
| 5,575,187 A | 11/1996 | Dieterlen |
| 5,586,964 A | 12/1996 | Chase |
| 5,602,747 A | 2/1997 | Rajala |
| 5,603,794 A | 2/1997 | Thomas |
| 5,616,113 A * | 4/1997 | Van Den Bergh .............. 493/23 |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| 5,683,531 A | 11/1997 | Roessler et al. |
| RE35,687 E | 12/1997 | Igaue et al. |
| 5,693,165 A | 12/1997 | Schmitz |
| 5,699,653 A * | 12/1997 | Hartman ................ B65B 9/087 493/9 |
| 5,705,013 A | 1/1998 | Nease |
| 5,707,470 A | 1/1998 | Rajala et al. |
| 5,711,832 A | 1/1998 | Glaug et al. |
| 5,716,311 A * | 2/1998 | Novick et al. .................. 493/32 |
| 5,725,518 A | 3/1998 | Coates |
| 5,725,714 A | 3/1998 | Fujioka |
| 5,743,994 A | 4/1998 | Roessler et al. |
| 5,745,922 A | 5/1998 | Rajala et al. |
| 5,746,869 A | 5/1998 | Hayden et al. |
| 5,749,989 A | 5/1998 | Linman et al. |
| 5,766,389 A | 6/1998 | Brandon et al. |
| 5,788,797 A | 8/1998 | Herrin et al. |
| 5,817,199 A | 10/1998 | Brennecke et al. |
| 5,829,164 A | 11/1998 | Kotischke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A | 3/1999 | Fukui et al. |
| 5,876,792 A | 3/1999 | Caldwell |
| 5,879,500 A | 3/1999 | Herrin et al. |
| 5,902,222 A * | 5/1999 | Wessman ...................... 493/439 |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Borresen et al. |
| 5,964,970 A | 10/1999 | Woolwine et al. |
| 6,022,443 A | 2/2000 | Rajala et al. |
| 6,024,682 A * | 2/2000 | Mandel et al. .................. 493/23 |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,138,436 A * | 10/2000 | Malin et al. .................. 53/133.4 |
| 6,171,432 B1 | 1/2001 | Brisebois |
| 6,183,576 B1 | 2/2001 | Couillard et al. |
| 6,195,850 B1 | 3/2001 | Melbye |
| 6,196,147 B1 * | 3/2001 | Burton et al. ........... 112/470.16 |
| 6,210,386 B1 | 4/2001 | Inoue |
| 6,212,859 B1 | 4/2001 | Bielik, Jr. et al. |
| 6,214,147 B1 | 4/2001 | Mortellite et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,586 B1 | 8/2001 | Yeo et al. |
| 6,276,587 B1 | 8/2001 | Boerresen |
| 6,284,081 B1 | 9/2001 | Vogt et al. |
| 6,287,409 B1 | 9/2001 | Stephany |
| 6,306,122 B1 | 10/2001 | Narawa et al. |
| 6,309,336 B1 | 10/2001 | Muessig et al. |
| 6,312,420 B1 | 11/2001 | Sasaki et al. |
| 6,314,333 B1 | 11/2001 | Rajala et al. |
| 6,315,022 B1 | 11/2001 | Herrin et al. |
| 6,319,347 B1 | 11/2001 | Rajala |
| 6,336,921 B1 | 1/2002 | Kato et al. |
| 6,358,350 B1 | 3/2002 | Glaug et al. |
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,431,038 B2 | 8/2002 | Couturier |
| 6,440,246 B1 | 8/2002 | Vogt et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,514,233 B1 | 2/2003 | Glaug |
| 6,521,320 B2 | 2/2003 | McCabe et al. |
| 6,523,595 B1 | 2/2003 | Milner et al. |
| 6,524,423 B1 | 2/2003 | Hilt et al. |
| 6,526,733 B1 * | 3/2003 | Schellenberg .......... B65B 41/18 493/11 |
| 6,533,879 B2 | 3/2003 | Quereshi et al. |
| 6,540,857 B1 | 4/2003 | Coenen et al. |
| 6,547,909 B1 | 4/2003 | Butterworth |
| 6,551,228 B1 | 4/2003 | Richards |
| 6,551,430 B1 | 4/2003 | Glaug et al. |
| 6,554,815 B1 | 4/2003 | Umebayashi |
| 6,557,466 B2 * | 5/2003 | Codde et al. .................. 101/216 |
| 6,569,275 B1 | 5/2003 | Popp et al. |
| 6,572,520 B2 | 6/2003 | Blumle |
| 6,581,517 B1 | 6/2003 | Becker et al. |
| 6,585,841 B1 | 7/2003 | Popp et al. |
| 6,589,149 B1 | 7/2003 | VanEperen et al. |
| 6,596,107 B2 | 7/2003 | Stopher |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Anderson |
| 6,648,122 B1 | 11/2003 | Hirsch et al. |
| 6,649,010 B2 | 11/2003 | Parrish et al. |
| 6,651,923 B2 | 11/2003 | Kinnunen et al. |
| 6,656,309 B1 | 12/2003 | Parker et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,684,925 B2 | 2/2004 | Nagate et al. |
| 6,722,494 B2 | 4/2004 | Nakakado |
| 6,730,189 B1 | 5/2004 | Franzmann |
| 6,743,324 B2 | 6/2004 | Hargett et al. |
| 6,750,466 B2 | 6/2004 | Guha et al. |
| 6,758,109 B2 | 7/2004 | Nakakado |
| 6,766,817 B2 | 7/2004 | da Silva |
| 6,808,582 B2 | 10/2004 | Popp et al. |
| D497,991 S | 11/2004 | Otsubo et al. |
| 6,814,217 B2 | 11/2004 | Blumenthal et al. |
| 6,820,671 B2 | 11/2004 | Calvert |
| 6,837,840 B2 | 1/2005 | Yonekawa et al. |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,913,664 B2 * | 7/2005 | Umebayashi et al. .......... 156/64 |
| 6,913,718 B2 | 7/2005 | Ducker |
| 6,918,404 B2 | 7/2005 | Dias da Silva |
| 6,942,759 B2 | 9/2005 | Mohrsen et al. |
| 6,946,059 B2 | 9/2005 | Mohrsen et al. |
| 6,976,521 B2 | 12/2005 | Mlinar |
| 6,978,486 B2 | 12/2005 | Zhou et al. |
| 7,017,820 B1 | 3/2006 | Brunner |
| 7,045,031 B2 | 5/2006 | Popp et al. |
| 7,066,586 B2 | 6/2006 | da Silva |
| 7,077,393 B2 | 7/2006 | Ishida |
| 7,130,710 B2 | 10/2006 | Popp et al. |
| 7,144,356 B2 * | 12/2006 | Harnish .............................. 493/8 |

(56) References Cited

U.S. PATENT DOCUMENTS

| | | | |
|---|---|---|---|
| 7,172,666 B2 | 2/2007 | Groves et al. | |
| 7,195,684 B2 | 3/2007 | Satoh | |
| 7,201,345 B2 | 4/2007 | Werner | |
| 7,214,174 B2 | 5/2007 | Allen et al. | |
| 7,214,287 B2 | 5/2007 | Shiomi | |
| 7,247,219 B2 | 7/2007 | O'Dowd | |
| 7,303,708 B2 | 12/2007 | Andrews et al. | |
| 7,380,213 B2 | 5/2008 | Pokorny et al. | |
| 7,398,870 B2 | 7/2008 | McCabe | |
| 7,449,084 B2 | 11/2008 | Nakakado | |
| 7,452,436 B2 | 11/2008 | Andrews | |
| 7,500,941 B2 * | 3/2009 | Coe et al. | 493/438 |
| 7,533,709 B2 | 5/2009 | Meyer | |
| 7,537,215 B2 | 5/2009 | Beaudoin et al. | |
| 7,569,007 B2 * | 8/2009 | Thoma | 493/23 |
| 7,587,966 B2 | 9/2009 | Nakakado et al. | |
| 7,618,513 B2 | 11/2009 | Meyer | |
| 7,638,014 B2 | 12/2009 | Coose et al. | |
| 7,640,962 B2 | 1/2010 | Meyer et al. | |
| 7,703,599 B2 | 4/2010 | Meyer | |
| 7,708,849 B2 | 5/2010 | McCabe | |
| 7,770,712 B2 | 8/2010 | McCabe | |
| 7,771,407 B2 | 8/2010 | Umebayashi | |
| 7,780,052 B2 | 8/2010 | McCabe | |
| 7,809,179 B2 | 10/2010 | Singh et al. | |
| 7,811,403 B2 | 10/2010 | Andrews | |
| 7,861,756 B2 | 1/2011 | Jenquin et al. | |
| 7,871,400 B2 | 1/2011 | Sablone et al. | |
| 7,909,956 B2 | 3/2011 | Coose et al. | |
| 7,975,584 B2 | 7/2011 | McCabe | |
| 7,987,964 B2 | 8/2011 | McCabe | |
| 8,007,484 B2 | 8/2011 | McCabe et al. | |
| 8,007,623 B2 | 8/2011 | Andrews | |
| 8,011,493 B2 | 9/2011 | Giuliani et al. | |
| 8,016,972 B2 | 9/2011 | Andrews et al. | |
| 8,257,535 B2 | 9/2012 | Yamamoto | |
| 8,273,003 B2 * | 9/2012 | Umebayashi et al. | 493/417 |
| 2001/0012813 A1 | 8/2001 | Bluemle | |
| 2001/0017181 A1 | 8/2001 | Otruba et al. | |
| 2002/0046802 A1 | 4/2002 | Tachibana et al. | |
| 2002/0059013 A1 | 5/2002 | Rajala et al. | |
| 2002/0084568 A1 * | 7/2002 | Codde et al. | 270/37 |
| 2002/0096241 A1 | 7/2002 | Instance | |
| 2002/0125105 A1 | 9/2002 | Nakakado | |
| 2002/0162776 A1 | 11/2002 | Hergeth | |
| 2003/0000620 A1 | 1/2003 | Herrin et al. | |
| 2003/0015209 A1 | 1/2003 | Gingras et al. | |
| 2003/0051802 A1 | 3/2003 | Hargett et al. | |
| 2003/0052148 A1 | 3/2003 | Rajala et al. | |
| 2003/0066585 A1 | 4/2003 | McCabe | |
| 2003/0083638 A1 | 5/2003 | Molee | |
| 2003/0084984 A1 | 5/2003 | Glaug et al. | |
| 2003/0089447 A1 | 5/2003 | Molee et al. | |
| 2003/0121614 A1 | 7/2003 | Tabor et al. | |
| 2003/0135189 A1 | 7/2003 | Umebayashi | |
| 2004/0007328 A1 | 1/2004 | Popp et al. | |
| 2004/0016500 A1 | 1/2004 | Tachibana et al. | |
| 2004/0044325 A1 | 3/2004 | Corneliusson | |
| 2004/0087425 A1 | 5/2004 | Ng et al. | |
| 2004/0112517 A1 | 6/2004 | Groves et al. | |
| 2004/0164482 A1 | 8/2004 | Edinger | |
| 2004/0182497 A1 | 9/2004 | Lowrey | |
| 2005/0000628 A1 | 1/2005 | Norrby | |
| 2005/0022476 A1 | 2/2005 | Hamer | |
| 2005/0026760 A1 * | 2/2005 | Yamamoto et al. | 493/81 |
| 2005/0077418 A1 | 4/2005 | Werner et al. | |
| 2005/0139713 A1 | 6/2005 | Weber et al. | |
| 2005/0196538 A1 | 9/2005 | Sommer et al. | |
| 2005/0230056 A1 | 10/2005 | Meyer et al. | |
| 2005/0230449 A1 | 10/2005 | Meyer et al. | |
| 2005/0233881 A1 | 10/2005 | Meyer | |
| 2005/0234412 A1 | 10/2005 | Andrews et al. | |
| 2005/0257881 A1 | 11/2005 | Coose et al. | |
| 2005/0275148 A1 | 12/2005 | Beaudoin et al. | |
| 2006/0021300 A1 | 2/2006 | Tada et al. | |
| 2006/0137298 A1 | 6/2006 | Oshita et al. | |
| 2006/0199718 A1 * | 9/2006 | Thoma | 493/424 |
| 2006/0217253 A1 * | 9/2006 | Thoma | B65H 45/16 493/432 |
| 2006/0224137 A1 | 10/2006 | McCabe et al. | |
| 2006/0265867 A1 | 11/2006 | Schaap | |
| 2007/0045461 A1 | 3/2007 | Sartain et al. | |
| 2007/0074953 A1 | 4/2007 | McCabe | |
| 2007/0238596 A1 * | 10/2007 | Terhaag et al. | 493/433 |
| 2008/0223537 A1 | 9/2008 | Wiedmann | |
| 2009/0020211 A1 | 1/2009 | Andrews et al. | |
| 2010/0078119 A1 | 4/2010 | Yamamoto | |
| 2010/0078120 A1 | 4/2010 | Otsubo | |
| 2010/0078127 A1 | 4/2010 | Yamamoto | |
| 2010/0168708 A1 * | 7/2010 | Umebayashi | A61F 13/15747 604/385.03 |
| 2010/0193138 A1 | 8/2010 | Eckstein | |
| 2010/0193155 A1 | 8/2010 | Nakatani | |

FOREIGN PATENT DOCUMENTS

| | | |
|---|---|---|
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 10/2006 |
| CA | 2559517 | 4/2007 |
| CA | 2337700 | 8/2008 |
| CA | 2407867 | 6/2010 |
| DE | 60123502 | 10/2006 |
| DE | 60216550 | 12/2006 |
| DE | 102005048868 | 4/2007 |
| DE | 102006047280 | 4/2007 |
| EP | 0044206 | 1/1982 |
| EP | 0048011 | 3/1982 |
| EP | 0089106 | 9/1983 |
| EP | 0099732 | 2/1984 |
| EP | 0206208 | 12/1986 |
| EP | 0304140 | 2/1989 |
| EP | 0439897 | 8/1991 |
| EP | 0455231 A1 | 11/1991 |
| EP | 510251 | 10/1992 |
| EP | 0652175 A1 | 5/1995 |
| EP | 0811473 | 12/1997 |
| EP | 0901780 | 3/1999 |
| EP | 0990588 | 4/2000 |
| EP | 1132325 A2 | 9/2001 |
| EP | 1199057 | 4/2002 |
| EP | 1272347 | 1/2003 |
| EP | 1366734 | 12/2003 |
| EP | 1504738 A2 | 2/2005 |
| EP | 1571249 | 9/2005 |
| EP | 1619008 | 1/2006 |
| EP | 1707168 A2 | 10/2006 |
| EP | 1726414 | 11/2006 |
| EP | 1302424 | 12/2006 |
| EP | 1801045 | 6/2007 |
| EP | 1941853 | 7/2008 |
| EP | 2233116 | 9/2010 |
| EP | 2238955 | 10/2010 |
| ES | 509706 | 11/1982 |
| ES | 520559 | 12/1983 |
| ES | 296211 | 12/1987 |
| ES | 200601373 | 7/2009 |
| ES | 2331349 | 9/2009 |
| FR | 2177355 | 11/1973 |
| FR | 2255961 | 7/1975 |
| FR | 1132325 | 10/2006 |
| FR | 2891811 | 4/2007 |
| GB | 191101501 A | 0/1912 |
| GB | 439897 | 12/1935 |

(56) References Cited

FOREIGN PATENT DOCUMENTS

| | | |
|---|---|---|
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| IT | 1374910 | 5/2010 |
| IT | 1374911 | 5/2010 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 A | 7/1994 |
| JP | 9299398 | 11/1997 |
| JP | 10035621 | 2/1998 |
| JP | 10-277091 A | 10/1998 |
| SE | 0602047 | 5/2007 |
| SE | 0601003-7 | 6/2007 |
| SE | 0601145-6 | 10/2009 |
| WO | WO9403301 | 2/1994 |
| WO | WO9732552 | 9/1997 |
| WO | WO9747265 | 12/1997 |
| WO | WO9747810 | 12/1997 |
| WO | WO9821134 | 5/1998 |
| WO | WO9907319 | 2/1999 |
| WO | WO9913813 A1 | 3/1999 |
| WO | WO9932385 | 7/1999 |
| WO | WO9965437 | 12/1999 |
| WO | WO0143682 | 6/2001 |
| WO | WO0172237 A2 | 10/2001 |
| WO | WO2004007329 | 1/2004 |
| WO | WO2005075163 | 8/2005 |
| WO | WO2007029115 | 3/2007 |
| WO | WO2007039800 | 4/2007 |
| WO | WO2007126347 | 11/2007 |
| WO | WO2008001209 | 1/2008 |
| WO | WO2008155618 | 12/2008 |

OTHER PUBLICATIONS

USPTO Office Action regarding U.S. Appl. No. 11/880,261, dated Jul. 23, 2009, 14 pages.
USPTO Office Action regarding U.S. Appl. No. 11/880,261, dated Mar. 10, 2010, 11 pages.
USPTO Office Action regarding U.S. Appl. No. 11/880,261, dated Nov. 9, 2010, 14 pages.
USPTO Office Action regarding U.S. Appl. No. 11/880,261, dated Jun. 23, 2011, 10 pages.
USPTO Office Action regarding U.S. Appl. No. 11/880,261, dated Jan. 5, 2012, 8 pages.
"Reciprocating Mechanisms", Franklin Jones, vol. 1, date unknown, 2 pages.
European Search Report regarding Application No. EP11250709, dated Oct. 17, 2014, 9 pages.

* cited by examiner

APPARATUS AND METHOD FOR MINIMIZING WASTE AND IMPROVING QUALITY AND PRODUCTION IN WEB PROCESSING OPERATIONS BY AUTOMATIC CUFF DEFECT CORRECTION

RELATED APPLICATIONS

This application claims the benefit of U.S. Provisional Patent Application Ser. No. 61/400,969, filed 5 Aug. 2010.

BACKGROUND OF THE INVENTION

The invention disclosed herein relates to apparatus and methods for waste reduction and improvements to the quality and production in web processing operations, such as diaper manufacturing. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll. Examples of web accumulators include that disclosed in U.S. patent application Ser. No. 11/110,616, which is commonly owned by the assignee of the present application, and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

SUMMARY OF THE INVENTION

Provided are method and apparatus for minimizing waste and improving quality and production in web processing operations.

Importantly, the methods taught in the present application are applicable not only to diapers and the like, but in any web based operation. The waste minimization techniques taught herein can be directed any discrete component of a manufactured article, i.e., the methods taught herein are not product specific. For instance, the present methods can be applied as easily with respect to diaper components as they can for feminine hygiene products, as they can for face masks in which components such as rubber bands and nose pieces are used.

For instance, by practicing the methods of the present invention, waste of staples and elastic bands can be avoided during manufacture of face masks, for instance those disclosed in U.S. Pat. No. 7,131,442. One of the objectives is simply to recognize product during manufacture that ultimately would fail quality control inspection, and avoid placing material on to that product during the manufacturing processes.

As another example, the amount of adhesive applied to certain products can be reduced by not applying adhesive to products that have already been determined to be defected or assigned to rejection. For instance, in U.S. Pat. No. 6,521, 320, adhesive application is shown for example in FIG. 11. By assigning or flagging product that has already been determined to end up in a scrap or recycling pile, the adhesive flow can be stopped or minimized.

In yet another exemplary application of the methods of the present invention, discrete components or raw material carried on products that have already been determined to be defected or assigned to rejection can also be removed and recycled prior to commingling with other discrete components or raw material. For instance, if an absorbent pad, such as shown at reference numeral 40 of U.S. Pat. No. 6,521,320 is destined for application to a product that has already been determined to be defected or assigned to rejection, the absorbent pad can be withdrawn from the product, or never introduced in the first instance. For example, during startup or shutdown of high speed diaper manufacturing operations, a certain number of products is routinely discarded into recycling. By identification of the start up or shut down routine, avoidance of introduction of absorbent pads can be achieved. Alternatively, during stand-by, the absorbent pads often degrade by accumulation of dust. By identifying which products would bear the dust, the absorbent pads can be withdrawn from further manufacture, and no additional components would be applied to such a product.

In one embodiment, a method for assembling a plurality of continuous webs is provided, including defining first web inspection parameters and inspecting at least one of the plurality of continuous webs to determine whether the at least one web conforms to the first web inspection parameters. Further, the method involves providing a chassis web which is adapted to receive a patch and providing a patch web from which the patch is cut. Finally, the cut patch is applied to the chassis web if the inspected web conforms to the first web inspection parameters. In another embodiment, the method also includes steps of defining first patch inspection parameters and inspecting a cut patch to determine whether the patch conforms to the first patch inspection parameters. While the patch inspection may provide interesting diagnostic information related to a web processing machine, the application of the patch may be limited to those patches that conform to the first patch inspection parameters.

Another embodiment of the method of the present invention involves defining first web inspection parameters and a product pitch. Generally in any web process, a web is provided, which is traveling at a web velocity. This embodiment involves inspecting the web to determine whether the web conforms to the first web inspection parameters and producing an inspection value as a result of the inspecting step. This value is then recorded once per sample time interval. The sample time interval may be calculated by dividing the defined product pitch by the web velocity. While the inspection value may be as simple as a bivalent value, a more informational multivalent value may be used.

In addition to the web process provided, an apparatus for carrying out the process is provided. An embodiment of the apparatus includes a continuous web supply providing continuous web material from an upstream position to a downstream position and a means for providing a patch spaced from a first side of the continuous web material. A patch applicator is provided to alter the space between the patch providing means and the continuous web material and a web inspection device is positioned upstream from the patch applicator. Additionally, a programmable controller receives an input from the web inspection device and provides an output to the patch applicator. The web processing apparatus may also include a patch inspection device that provides an output to the programmable controller. A patch reject conveyor may be positioned to receive defective patches from the patch providing means. In another embodiment of a web processing apparatus, a product inspection device may be located downstream from the patch applicator to provide an output to the programmable controller. Also, a product reject conveyor could be adapted to divert defective product as indicated by the product inspection device.

One aspect of the present invention involves automatically correcting any cuff folding defects. Before entering the cuff folding system, the cuff material is first slit into two even width strips and then passes through a web guide. The cuff fold is created by passing the material over the elastic guide roller. Part of the cuff web extends over the edge of the elastic guide roller; it is this portion of cuff that is folded back on top of itself. As the cuff web passes over the elastic roller guide, two adhesive coated strands of elastic are laid down on top of the cuff web just before folding. The fold is completed as the cuff passes over the folding board with the elastic strands inside the fold. The cuff next passes over the chill roll to set the adhesive. During the folding of the cuff non-woven, the non-woven can become operatively disengaged with the plow, causing the overlap not to be formed, resulting in a product defect by which the cuff elastic is not captured within a pocket in the non-woven.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present waste minimization techniques and apparatus are described herein with respect to products such as diapers, but as previously mentioned, can be applied to a wide variety of processes in which discrete components are applied sequentially.

Figure 1:
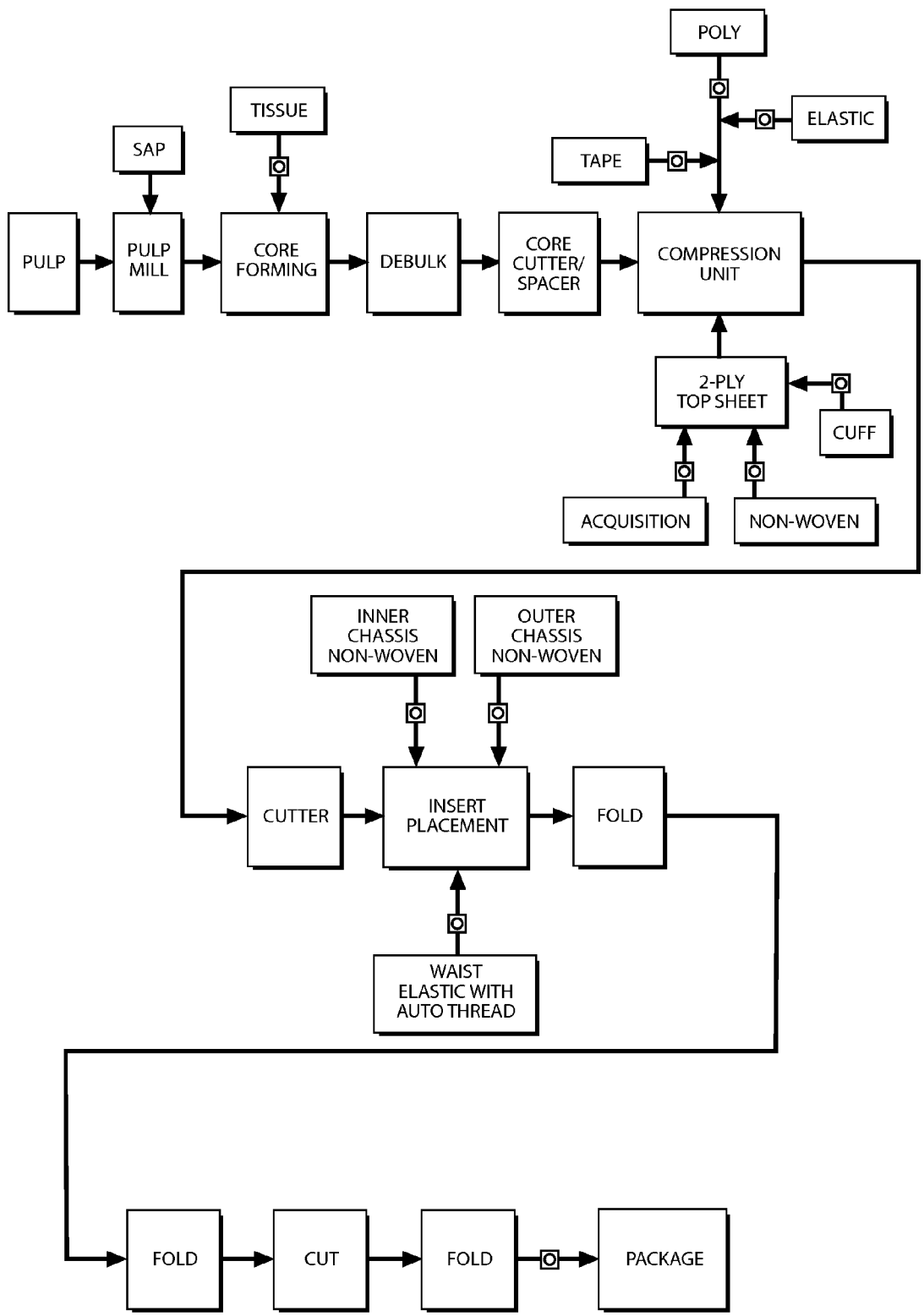
FIG. 1 is a schematic of a representative web processing system.

Referring to FIG. 1, a web processing operation starts with incorporating raw materials such as paper pulp and super absorbent polymer (SAP) in a pulp mill. The mixture is sent to a core forming drum, where cores are formed for retaining liquids. A core can be placed on a tissue and processed as shown. Eventually, an additional tissue layer is formed, sandwiching the core.

The process continues through debulking, core cutting and spacing, optionally, compression, and application of tape and elastics. The process then proceeds with application of outer and inner non-woven layers, and waist elastic. The web can undergo folding, extraction and trimming of excess material, and application of material to tighten the diaper about the waist. Eventually, the product is folded and packaged.

As seen on FIG. 1, the  symbol is shown at locations of introductions of discrete components into the process. At these locations, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

Figure 2A:
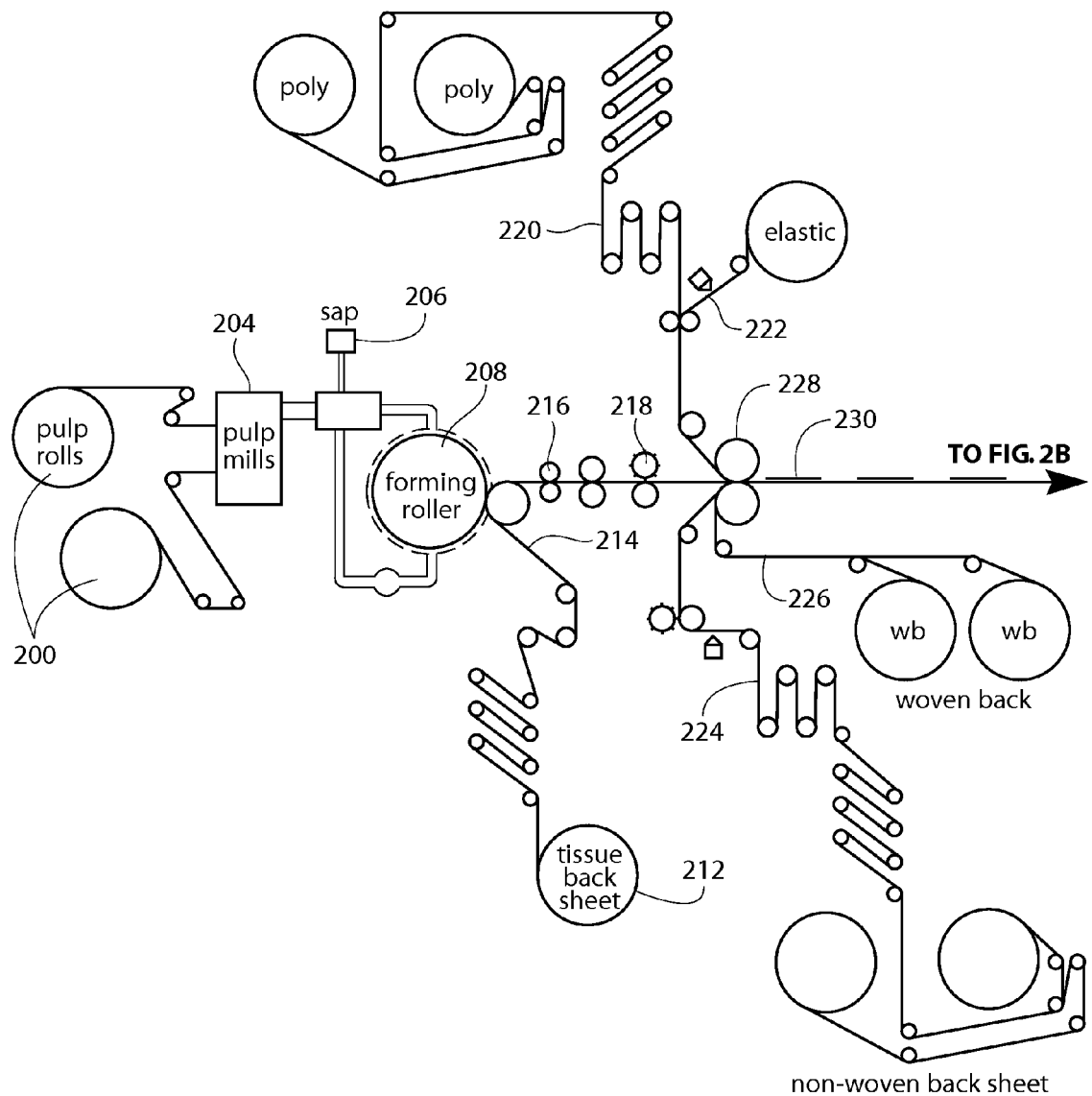
FIG. 2A-2C are schematic representations of a web processing system incorporating principles of the present invention.
Figure 2B:
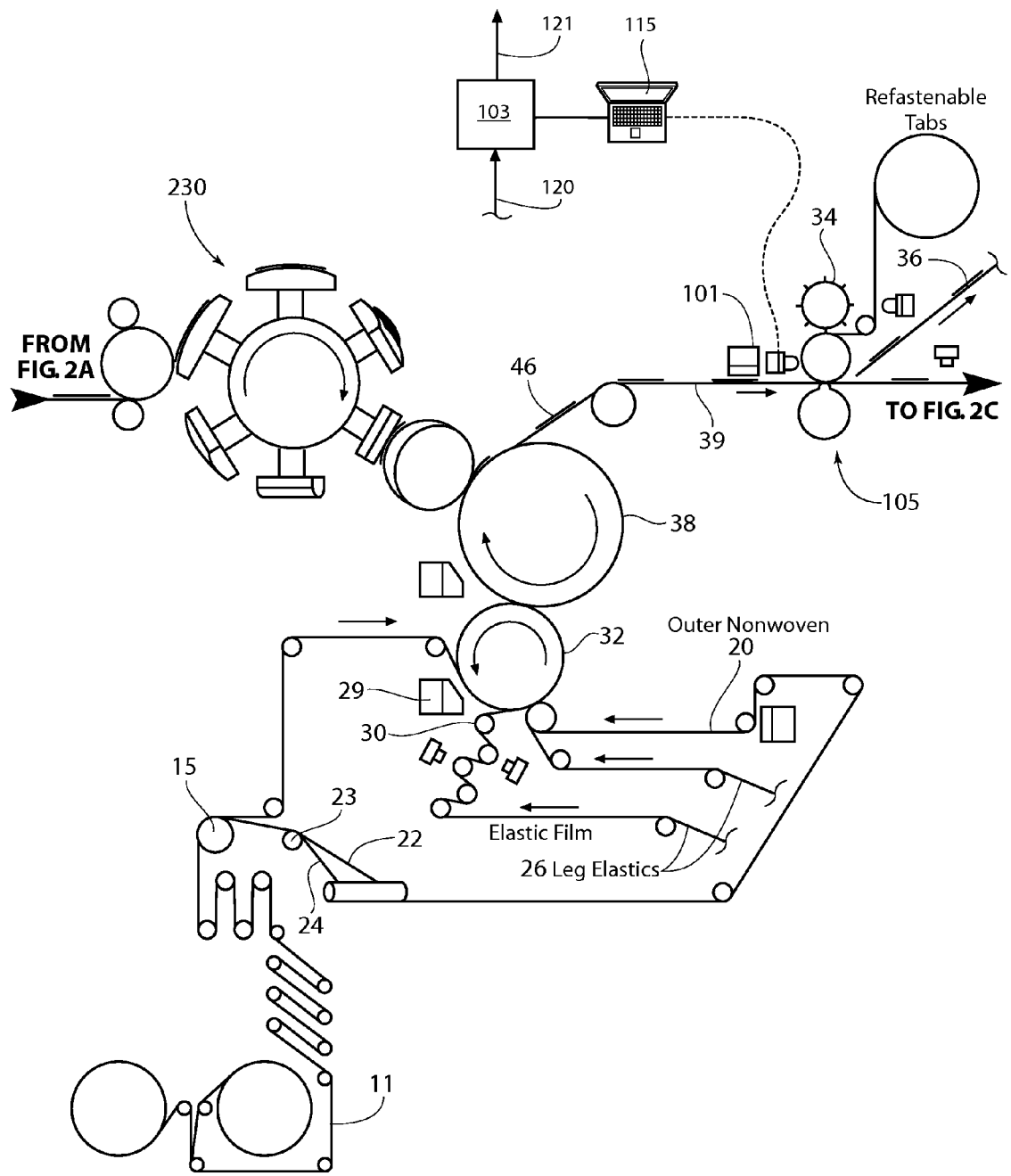
Figure 2C:
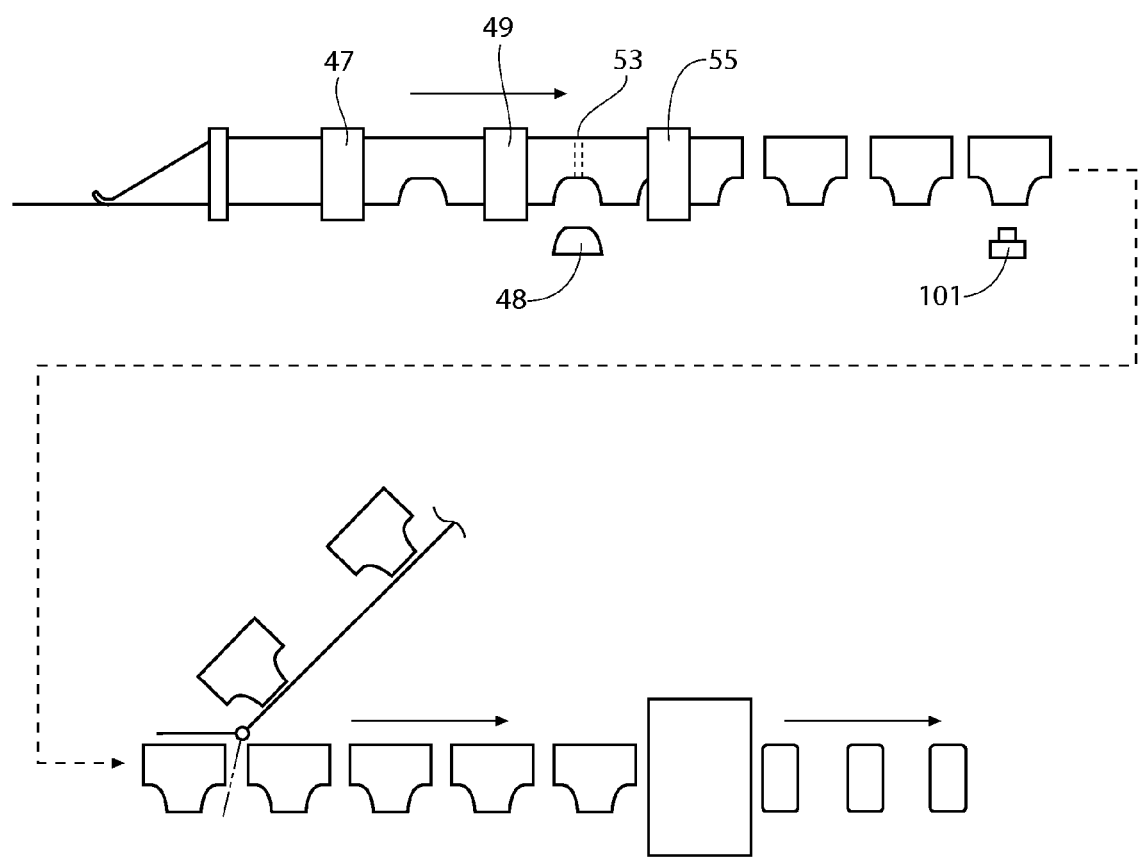

Referring now to FIGS. 2a-c, a web processing operation incorporating the present invention is shown.

Referring now to FIG. 2, an additional schematic of processes of the present invention is shown. As indicated, pulp rolls 200 feed raw pulp 201 into a pulp mill 204, where the pulp is pulverized. Super absorbent polymer is added from station 206. The SAP laced pulp is fed onto core forming roller 208. Cores 210 from core forming roller 208 are applied to the tissue back sheet 214 which has been introduced through tissue back sheet feeder 212. Following debulking station 216 and core cutting and spacing station 218, an infeed of poly layer 220, elastic layer 222 is applied to the carrier web, in addition to non woven layer 224 and two ply top sheet woven 226. This web then is cut at cutting station 228 into discrete inserts 230, which are then typically placed on a article transfer and placement apparatus with active puck 230, such as that disclosed in U.S. Pat. No. 7,770,712, owned by the same assignee as the present case, and which is incorporated herein by reference.

The process utilizes two main carrier webs; a nonwoven web 11 which forms an inner liner web, and a web 12 that forms an outwardly facing layer in the finished diaper 50. In this embodiment, the nonwoven web 11 is slit, at slitter station 15, by rotary knives 14 along three lines. One of these lines is preferably on approximately the centerline of web 11 and the other two lines are parallel to and spaced a short distance from the centerline. The effect is twofold; first, to separate web 11 into two inner liners 20. One liner will become the inside of the front of the diaper 50 and the second liner will become the inside of the back of that garment. Second, two separate, relatively narrow strips 22 and 24 are formed which are subsequently used to cover and entrap portions of leg-hole elastics 26. Strips 22 and 24 are separated physically by an angularly disposed spreader roll 23 and aligned laterally with their downstream target positions on the inner edges of the liner webs 20.

Adhesive patterns are applied to the liner webs 20 in target areas for the leg-hole elastics 26. A spray gun assembly 29 of a type known in the art is preferably used to apply the adhesive patterns. Two sets of leg-hole, elastic strands 26 are introduced through laydown guides 30, which reciprocate from side to side past each other. The strands 26 are glued to the web sections 20, their laydown patterns following a serpentine path. Given the absence of adhesive in the area separating the inner liners 20, for some portion of each successive diaper product, the strands 26 each track parallel to the inner slit edges of the web sections 20. Laydown guides 30 then apply the strands 26, which form leg-hole elastics as the web sections 20 are carried along the face of a drum or roll 32. Those parts of the elastic patterns which are near the inner slit edges of webs 20 are then covered by the introduction of an adhesive lamination thereover of the strips 22 and 24 of nonwoven web also against the drum 32.

The side-to-side excursions of the leg-hole elastic laydown guides 30 result in arcuate segments of elastic strands extending on each side of the web centerline. After the nonwoven strips 22 and 24 have been applied to cover and entrap those parts of the elastics 26 that run nearest to and parallel to the inner edges of the webs 20, a second pair of slitter knives 34 is used to trim away a portion of the narrow nonwoven strips 22, 24, along with that part of the inner liner webs 20 to which they are laminated. This also removes those portions of the elastic strands 26 which are contained within the laminations. The resultant trimmed scrap strips 36 are removed from the process for disposal elsewhere.

The effect of the last-described step is to remove the cut away portions of the elastic, eliminating its corresponding unwanted gathering effect from the crotch region of the garments 50. The remaining portions of the curved elastic strands create a gathering effect around the leg openings of the finished garments 50.

Subsequent to the combining and trimming of the inner webs 20 and the cover strips 22, 24, the combining drum 32 carries the webs to a nip with a second combining drum 38, where the web sections 20, with their respective curved elastic patterns exposed, are transferred to and laminated adhesively against the inside face of outer liner web 12. This process entraps the curved elastic patterns 26 between the inner liners 20 and outer web 12 thereby forming a composite web 39.

The composite web 39 is then provided with a pattern of adhesive in preparation to receive an absorbent insert or patch 46. The patch 46 is cut from a provided patch web 40 by a cooperation of a cutter 41 and an anvil surface on a vacuum roll 42 and rotated into position for transfer to the composite web 39 by a patch applicator 105. If the patch 46 is to be applied to the web 39—a determination explained more fully below—the patch applicator 105 forces the web 39 against the patch 46, thereby adhering the patch 46 to the web 39.

Leg-hole materials 48, if not previously removed, are cut at a cutting station 47, thereby removing the material 48 contained within an approximate perimeter defined by the curved pattern of the elastics 26. The running composite chassis web 39 is folded, before or after cutting out of the leg holes, longitudinally along its centerline, thereby generally aligning its front waist edge with its back waist edge. The regions 53 which are to become the side seams 54 of the garments 50 are then welded by a sealing device 49 either ultrasonically or by heat. Note that the leg holes are preferably cut out before this point, leaving only a narrow zone for welding. The weld pattern is preferably wide enough to extend into both the left side seam of one garment and the right side seam of the adjacent garment. The garments 50 are then separated by passing through a cut-off knife assembly 55, which severs the web along the transverse axis of the side seam weld 53.

In addition to the exemplary components generally found in a web processing apparatus, the present device and methods further include an advanced defect detection system. An embodiment of the defect detection system preferably comprises at least one visual inspection station 101, but preferably a plurality of visual inspection stations 101. Each visual inspection station 101 may include a vision sensor, such as an In-Sight Vision Sensor available from Cognex Corporation of Natick, Mass. Since each component part of a product resulting from a web process has a point of incorporation into the product, visual inspection of each component part preferably occurs prior to the point of incorporation. The results of the visual inspections that occur are relayed from each visual inspection station 101 to a programmable logic controller (PLC) 103. Each visual inspection station 101 may provide diagnostic capability by monitoring lighting, focus and positioning.

Machine vision systems typically require digital input/output devices and computer networks to control other manufacturing equipment, in this case the splicing unit.

A typical machine vision system will consist of several among the following components:

- One or more digital or analog camera (black-and-white or color) with suitable optics for acquiring images
- Lighting
- Camera interface for digitizing images (widely known as a "frame grabber")
- A processor (often a PC or embedded processor, such as a DSP)
- Computer software to process images and detect relevant features.
- A synchronizing sensor for part detection (often an optical or magnetic sensor) to trigger image acquisition and processing.
- Input/Output hardware (e.g. digital I/O) or communication links (e.g. network connection or RS-232) to report results
- Some form of actuators used to sort or reject defective parts.

The sync sensor determines when a part (often moving on a conveyor) is in position to be inspected. The sensor triggers the camera to take a picture of the part as it passes by the camera and often synchronizes a lighting pulse. The lighting used to illuminate the part is designed to highlight features of interest and obscure or minimize the appearance of features that are not of interest (such as shadows or reflections).

The camera's image can be captured by the framegrabber. A framegrabber is a digitizing device (within a smart camera or as a separate computer card) that converts the output of the camera to digital format (typically a two dimensional array of numbers, corresponding to the luminous intensity level of the corresponding point in the field of view, called pixel) and places the image in computer memory so that it may be processed by the machine vision software.

The software will typically take several steps to process an image. In this case, the image processing will result in either detection of the indicator material, or non-detection of the indicator material.

Commercial and open source machine vision software packages typically include a number of different image processing techniques such as the following:

Pixel counting: counts the number of light or dark pixels

Thresholding: converts an image with gray tones to simply black and white

Segmentation: used to locate and/or count parts

Blob discovery & manipulation: inspecting an image for discrete blobs of connected pixels (e.g. a black hole in a grey object) as image landmarks. These blobs frequently represent optical targets for machining, robotic capture, or manufacturing failure.

Recognition-by-components: extracting geons from visual input

Robust pattern recognition: location of an object that may be rotated, partially hidden by another object, or varying in size Barcode reading: decoding of 1D and 2D codes designed to be read or scanned by machines Optical character recognition: automated reading of text such as serial numbers Gauging: measurement of object dimensions in inches or millimeters Edge detection: finding object edges Template matching: finding, matching, and/or counting specific patterns.

In most cases, a machine vision system will use a sequential combination of these processing techniques to perform a complete inspection. A system that reads a barcode may also check a surface for scratches or tampering and measure the length and width of a machined component.

Additionally, machine downtime can be minimized by the provision of systems and methods for warning a machine operator of expected machine troubles so that scheduled maintenance can occur.

The PLC 103 includes software adapted to run several routines that may be initiated by some triggering event, such as an automatic detection of a defined condition or manual input by a machine operator. Some routines are run during machine setup while other routines are run during machine operation, while still other routines are run during machine diagnostics at some point during machine downtime.

The PLC 103 generally receives inputs 120 from the visual inspection stations 101, from the various machine components, or from manual input by a machine operator on an operator interface, or human machine interface (HMI) 115. Some of the inputs can also be from stations near the pulp rolls, pulp mills, forming rollers, or elsewhere in the system where inspection is present.

The HMI 115 provides an interface for user interaction with the web processing machinery and may comprise a pressure sensitive touch screen, a keyboard, a computer mouse, or even a wireless device providing such an interface. The PLC 103 preferably provides controlling outputs 121 to the patch applicator 105, the cutter 41 and vacuum roll 42, a patch reject conveyor 107 and a product reject conveyor 109.

The input to the PLC 103 from each inspection station 101 preferably comprises a defect indicator 111 that represents a detected web defect at a position in the process a number of patch placements from the patch applicator 105. That is, at any given time during machine operation, between any inspection station 101 and any patch applicator 105 in a web process, there exists material sufficient to produce a determinable number of products having a patch applied thereto. Therefore, a defect may be detected and flagged as corresponding to a specific product location throughout the process.

In determining whether a patch should be applied to a product by a patch applicator 105, the PLC 103 stores a product status indicator for each product in the process, preferably for each product between the product reject conveyor 109 and most remote visual inspection station 101. The status indicator accumulates defect indicators 111 from the inspection stations 101 to track the progress of a product through the process.

A preferred product status indicator is a byte of digital data, with each bit reflecting the defect indicator 111 for the tagged product from an inspection station 101. For example, the least significant bit in the status indicator may represent the defect indicator for the most remote visual inspection station 101. As the bit significance increases, so does the proximity of the respective inspection station 101 to the product reject conveyor 109. A byte of data would provide for the possibility of eight inspection stations, and specific tracking of defects at those inspection stations. To store the product status indicator, the PLC 103 preferably includes some volatile and some nonvolatile computer memory. The volatile memory may provide quicker access times during machine operation, while the nonvolatile memory could be used to store product status indicators when the machine is paused. The minimum amount of memory required by the PLC 103 is at least partly determined by the number of visual inspection stations 101 and the number of potential products in queue between the first visual inspection station 101 and the product reject conveyor 109. For example, if a web process utilizes eight visual inspection stations 101 and two hundred products could be in queue in any given time, a volatile memory of at least two hundred bytes would be required.

The visual inspection station outputs may be sampled synchronously, or the outputs may be asynchronously analyzed by the PLC 103. If synchronous, the outputs may be sampled at a rate equal to the speed of the traveling webs divided by the product pitch, or product size. To enable use of different product sizes in a given process, the sample timing of the inspection station results may be varied, accordingly.

In addition to synchronous sampling of the inspection station results, the results could be analyzed asynchronously, which may be advantageous if various materials are incorporated into the process at different rates. Asynchronous analysis of the outputs, however, may provide less visibility into the specific defects included in a completed product.

Figure 3:
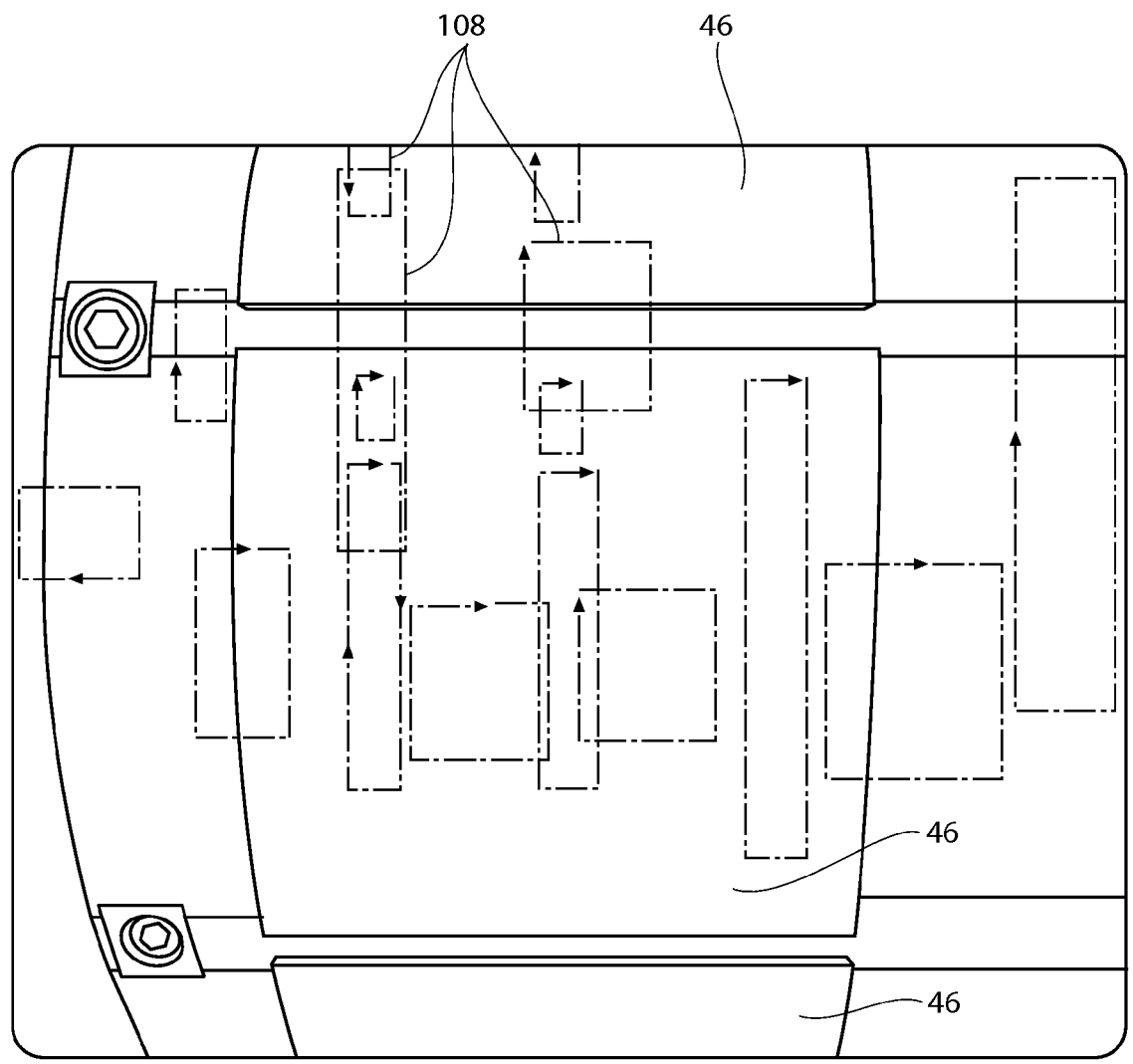
FIG. 3 is an elevation view of a patch inspection.

Prior to operating or running a web process, the machinery must be threaded with raw patch web material. The PLC 103 may provide a software routine, such as an automatic web threading routine, for aiding such setup. An operator threads the patch web material 40 through the machine to the patch applicator 105. The operator then initiates the automatic threading routine by using the HMI 115. The HMI 115 is coupled to the PLC 103 and the PLC 103 controls the patch applicator 105, patch cutter 41, vacuum roll 42, and patch reject conveyor 107. A first number of patches 46 are cut by the patch cutter 41 and culled via the patch reject conveyor 107. The culled patches 46a may be a predetermined number from the start of the threading routine, or cut patches 46 could be inspected by a visual inspection station 101, and culled until the patches 46 meet visual inspection parameters 108, as seen in FIG. 3.

Also, if the machine was shut down or paused with existing patch web material loaded through the patch cutter, but a vacuum remains drawn through the vacuum anvil drum, the patch web material on the vacuum anvil drum will act as an air filter. The longer the patch web material is on the drum, the dirtier it will get. Such soiled material may not be used in the construction of products for sale. Therefore, the PLC 103 could provide a software routine for clearing the vacuum anvil drum of soiled web material. Patches that have been on the anvil for a predetermined amount of time, and therefore may have dust built up, are culled through the reject prior to machine startup. Like the automatic threading routine, a predetermined number of patches may be culled, or the patches may be inspected for dust build-up.

In addition to threading and anvil clearing, a placement accuracy routine could be provided, for use on machine startup, or when the product configuration is changed. In a representative placement accuracy routine, patches are placed to several startup reject products, and relevant dimensions are taken by a visual inspection station 101 placed downstream from the patch applicator 105. The inspection results indicate if and when the patch placement meets specified patch placement parameters.

During machine operation, the PLC 103, through software algorithms, determines whether a patch 46 should be placed by the patch applicator 105, whether the patch 46 should be culled, or whether the web 39 should be allowed to continue to run without patch placement. A patch 46 is placed on the moving chassis web 39 only if both the patch 46 and web 39 are in condition for satisfactory placement.

After machine setup and threading of any materials, the PLC 103 begins verifying status indicators at the <application> position in memory. Generally, during machine operation, the PLC 103 controls whether a patch 46 is applied by a patch applicator 105. For each product, the PLC 103 determines the action of the patch applicator 105, the patch reject conveyor 107, and the product reject conveyor 109. For each product presented to a patch applicator 105, the PLC 103 issues one of the following commands to the patch applicator 105 and patch cutter: (1) apply patch; (2) cull patch; or (3) cull web.

The apply patch command is issued if no component part has been flagged as defective in the composite web 39 that is presented to the patch applicator 105 and the patch 46, itself, satisfies inspection parameters. When the apply patch command is issued, the vacuum anvil drum 42 remains relatively stationary while the composite web 39 having a deposited adhesive is forced by the patch applicator 105 against the patch 46. After the patch 46 is applied, the PLC awaits the arrival of the next patch attachment site or product pitch.

Figure 4:
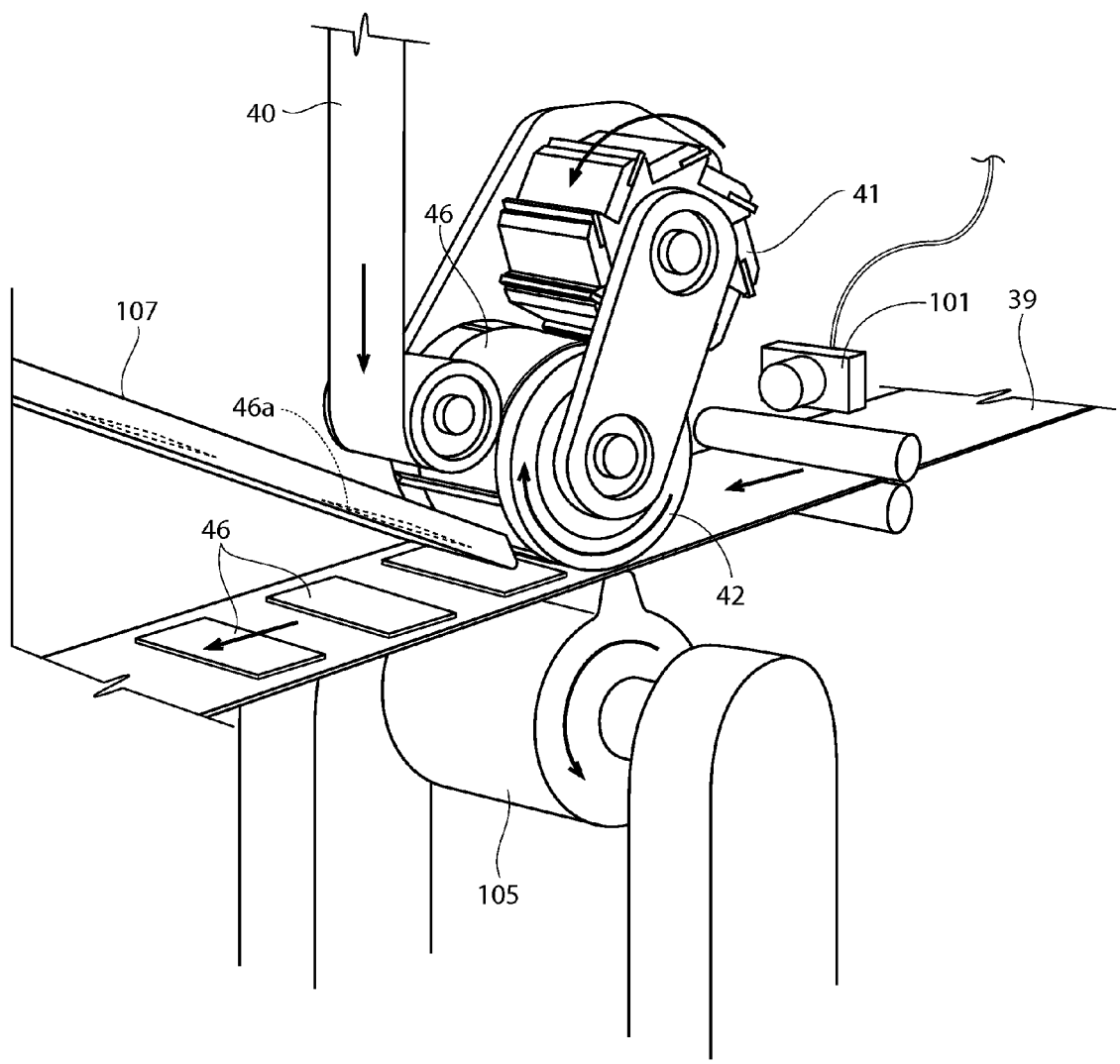
FIG. 4 is a perspective view of a patch indexer, a patch applicator and a patch reject conveyor.
Figure 5:
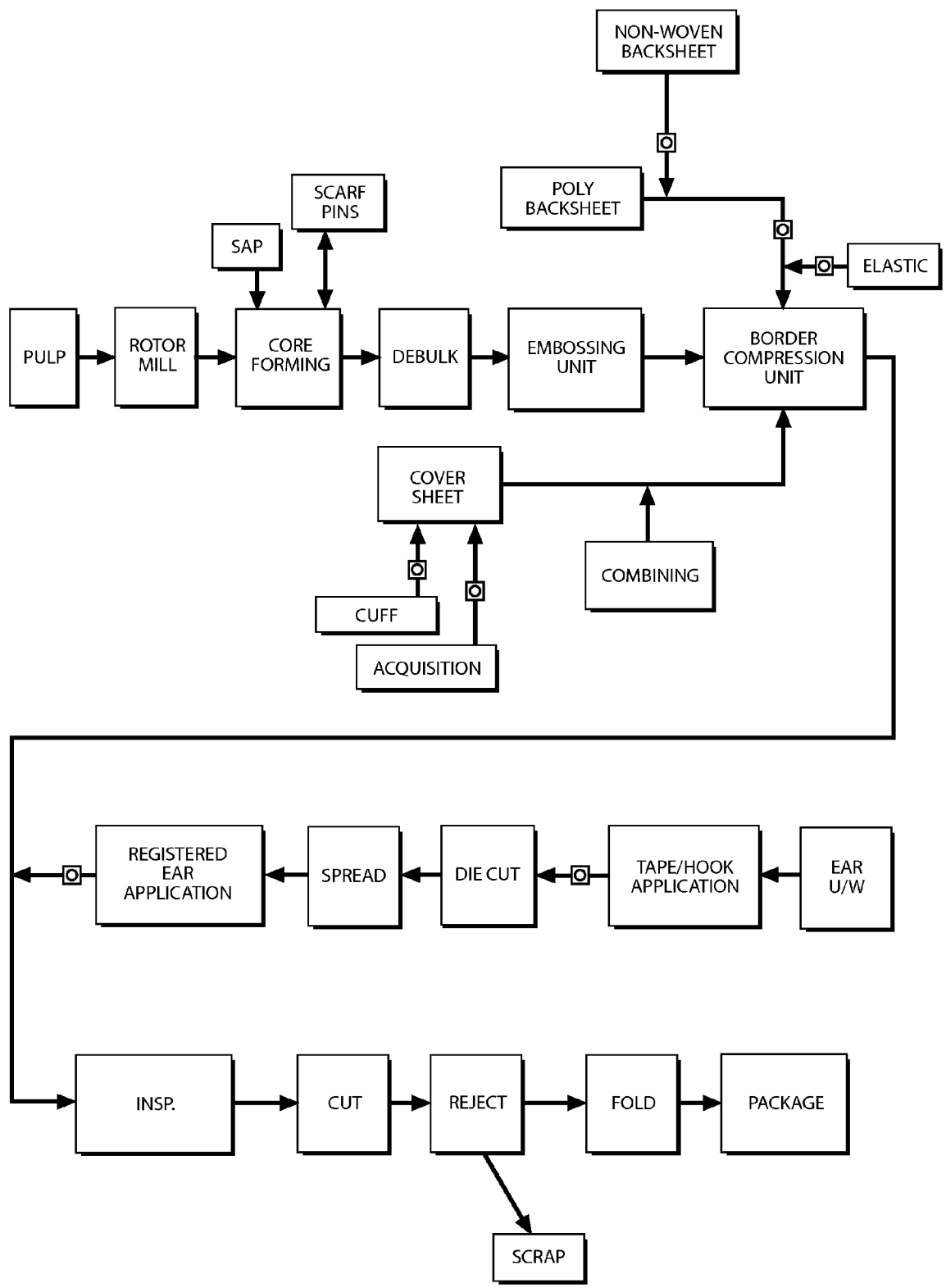
FIG. 5 is a schematic of a second embodiment of a representative web processing system.
Figure 6A:
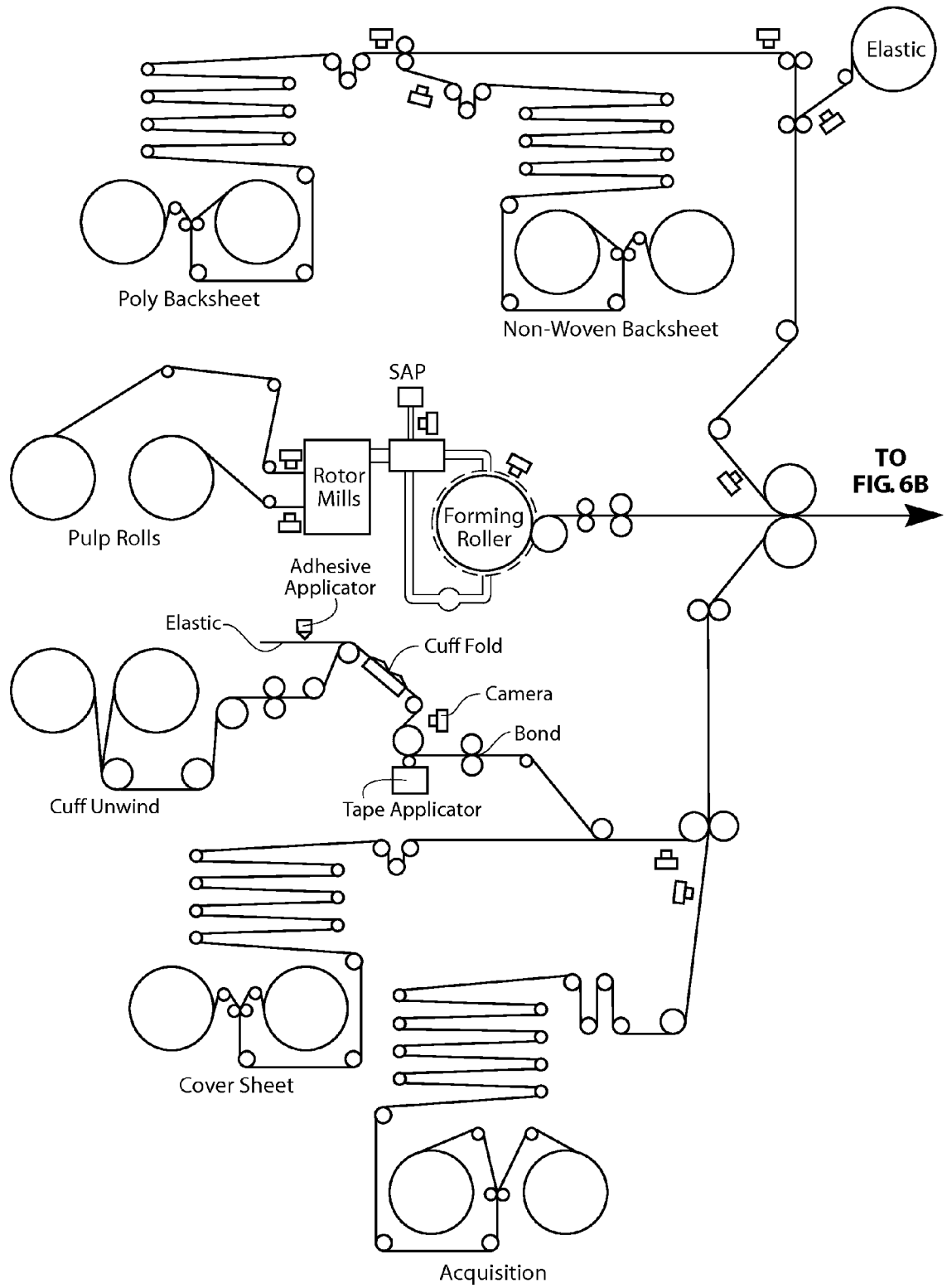
FIG. 6A-6C are additional schematic representations of a web processing system incorporating principles of the present invention.
Figure 6B:
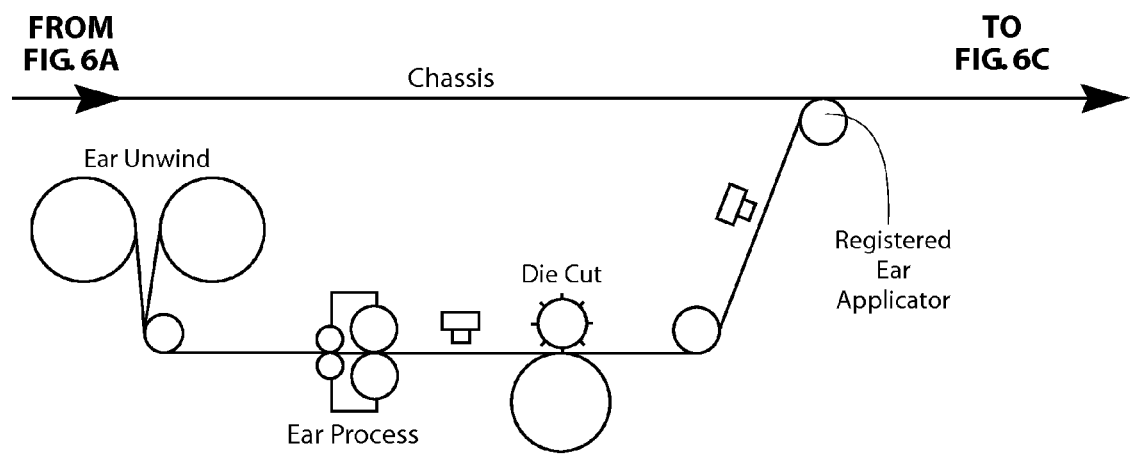
Figure 6C:
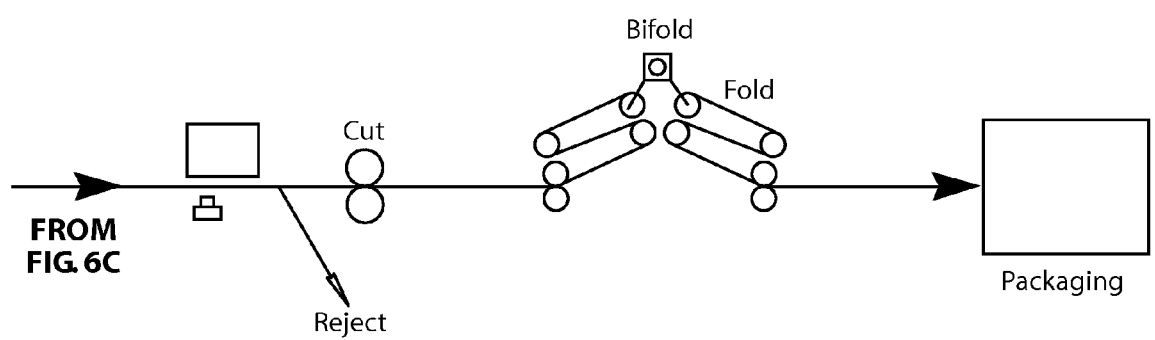

The cull patch command is issued if a patch 46a does not meet inspection parameters. Representative parameters can be seen in FIG. 4. Culling a defective patch 46a involves cooperation of the vacuum roll 42 and the patch reject conveyor 107. The vacuum roll 42 preferably has a vacuum manifold that allows a release of the vacuum draw at a certain point around the rotation path of the roll 42. The patch reject conveyor 107 may be a simple conveyor belt positioned just below the point where the vacuum draw may be removed, such that gravity causes the unapplied patch 46a to fall onto the conveyor 107.

The cull web command is issued if any component part of the composite web 39 is flagged as defective.

The PLC 103 may also contain a unit diagnostics program, which monitors parameters of the patch on the anvil to determine the health of the cutting knives and anvils. The unit diagnostics program involves the use of defined patch parameters measured by a vision inspection station and compared to expected values. Information that is gathered by the diagnostics program is stored and processed in a database. Where measured parameters are approaching acceptable limits, alerts are sent to the machine operator, indicating that potential problems are developing. The HMI may automatically present the Unit Diagnostics Screen for the operator to assess the situation. Furthermore, the HMI may provide graphics and charts to assist the operator by showing trend data, measured data, and comparable data. Thus, an operator is given advance notice of a problem so that any corrections can be made during the next machine downtime. Specifically, as the knives on the patch cutter age, the patches tend to skew. Furthermore, the deviation between subsequent patch cut lengths is another indicator that a knife blade may require replacement.

In an effort to prolong machine run-time between service and to reduce start-up rejects, an automatic anvil adjustment program may be provided. Such adjustment allows the anvil drum and knife roll to move relative to one another. Startup and shutdown rejects can result in rejections of many products. The movements are preferably in one millimeter increments over a five millimeter range. The adjustments are made as the machine is running to prevent wear on a single spot as well as to minimize buildup of cut web material on the anvil. In addition to the automatic adjustment, a manual override adjustment may be provided for troubleshooting.

If the unit diagnostics program detects a pair of patches that have parameters outside of acceptable limits, which is usually caused by a catastrophic failure of a knife or anvil, the machine operator is alerted and the HMI preferably automatically presents the Unit Diagnostics Screen for the operator to assess the situation. For every knife or anvil that fails, two patches will be affected. Therefore, if the anvil roller can accompany eight patches, twenty-five percent of the patches will fall out of acceptable limits. All patches that fall out of the acceptable limits are culled by way of the reject patch conveyor. All patches that fall within acceptable limits will continue to be placed on a composite web that is otherwise indicated as appropriate for receiving a patch. After being notified of the problem, the machine operator will observe the HMI to verify problem. In an attempt to correct the problem, the operator may try an electronic anvil shift, which, if successful, will allow the process to continue. If the electronic anvil shift does not correct the problem, the operator will request that the machine stop. To aid in repair or replacement of the failed knife or anvil, the cutter and anvil drum will stop in a position allowing easy access to the failed components. As a convenience and to enable more efficient repair of the failed components, a rapid change out (RCO) tool or kit could be provided, such as a set of hex wrenches. The operator changes the failed part and prepares the machine to restart. The routine for automatically clearing the anvil drum may then run, and the unit begins attaching patches to the composite web. The alarm that first alerted the operator of the problem is then reset, either automatically, or manually by the operator through the use of the HMI.

There may arise a situation where multiple anvils or knives appear to have failed. In this situation, the operator is alerted to the problem, but no patches are culled. Rather, a visual inspection station downstream from the patch applicator is examined to determine if there truly is a problem. If the problem is verified by the placement accuracy check, the operator shuts down the machine and proper maintenance is performed. If an examination of the placement accuracy inspection station does not confirm the purported problem, the unit diagnostics program may be suspended until it can be repaired.

Although the foregoing description involves the placement of an absorbent insert or patch onto a diaper chassis, it will be apparent to those skilled in the art that the apparatus and process could be used to avoid unnecessary waste in the application of any sort of patch to a moving web. Other examples of patches that may be placed are tape tab patches and reusable fasteners.

Referring now to FIGS. 5 and 6*a-c*, an additional embodiment of a representative web processing system is shown schematically and incorporating principles of the present invention. It is noted that throughout the web processing, inspection systems can be incorporated virtually anywhere, particularly at locations of raw material input into the process.

Automatic Cuff Folding Defect Correction

Figure 7:
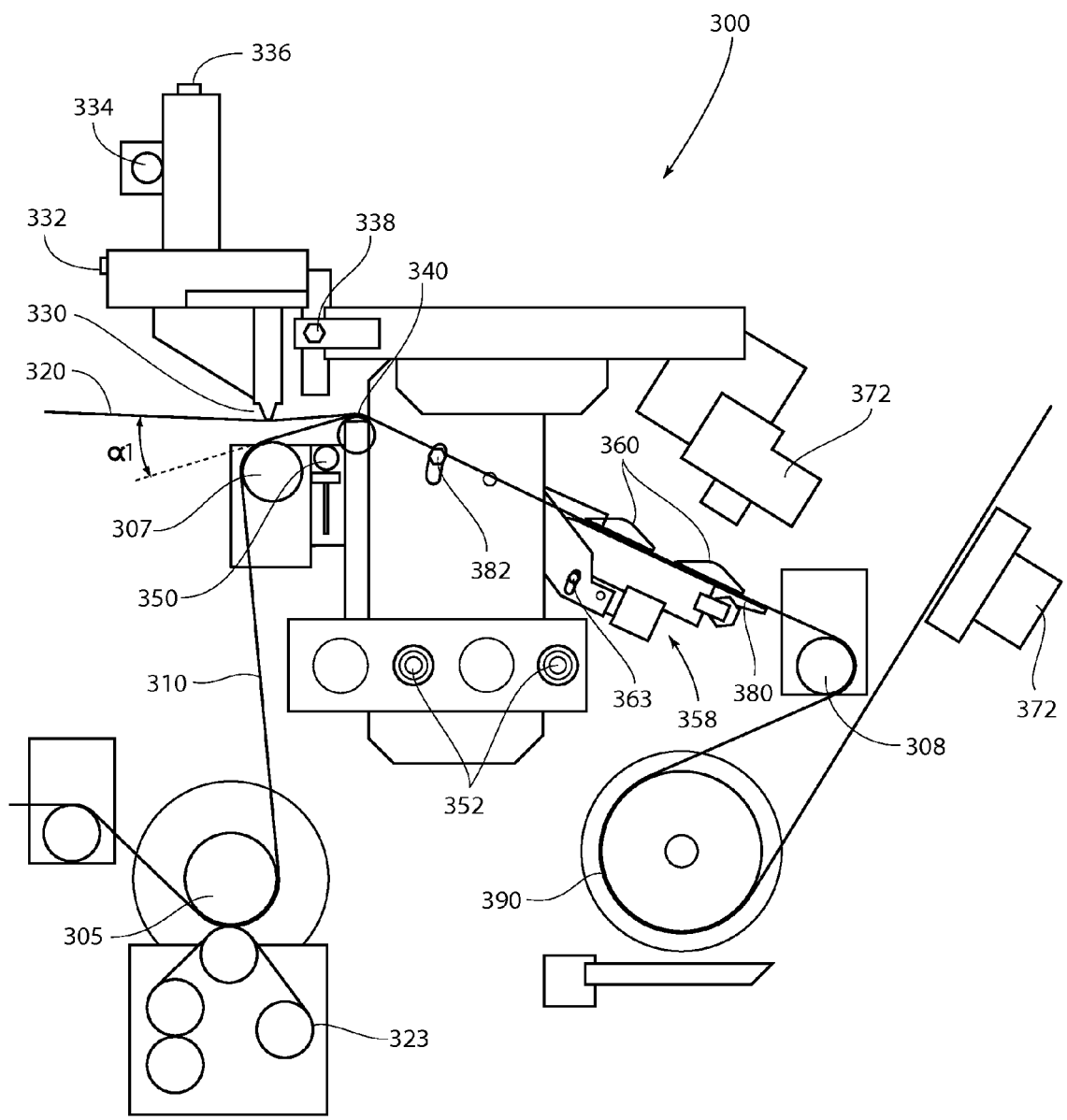
FIG. 7 is a side view of an automatic cuff defect correction system of the present invention.
Figure 8:
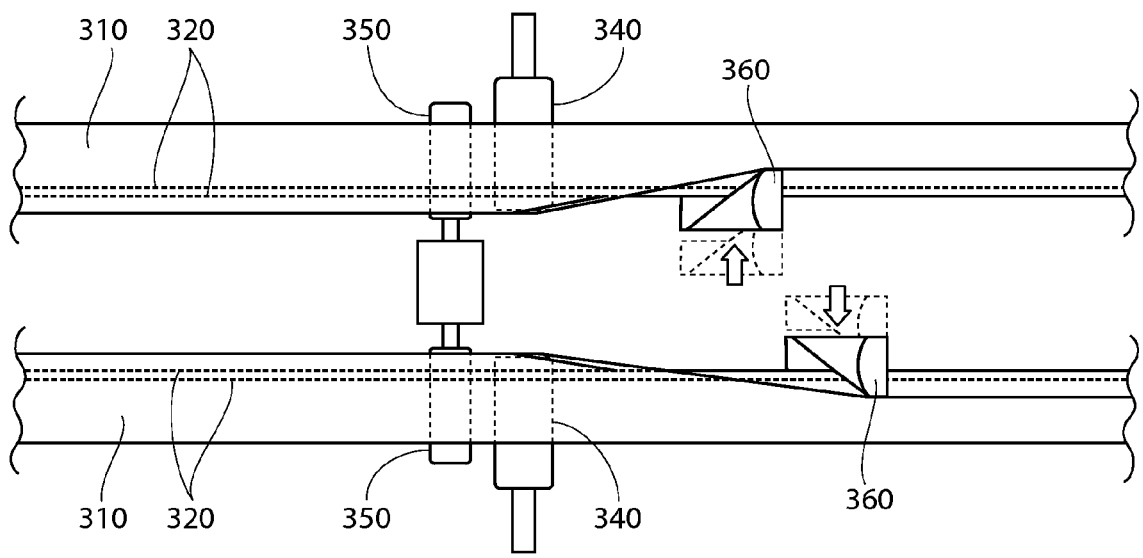
FIG. 8 is a top view of a retractable plow system used to assist, and a component of, an automatic cuff defect correction system of the present invention.
Figure 9:
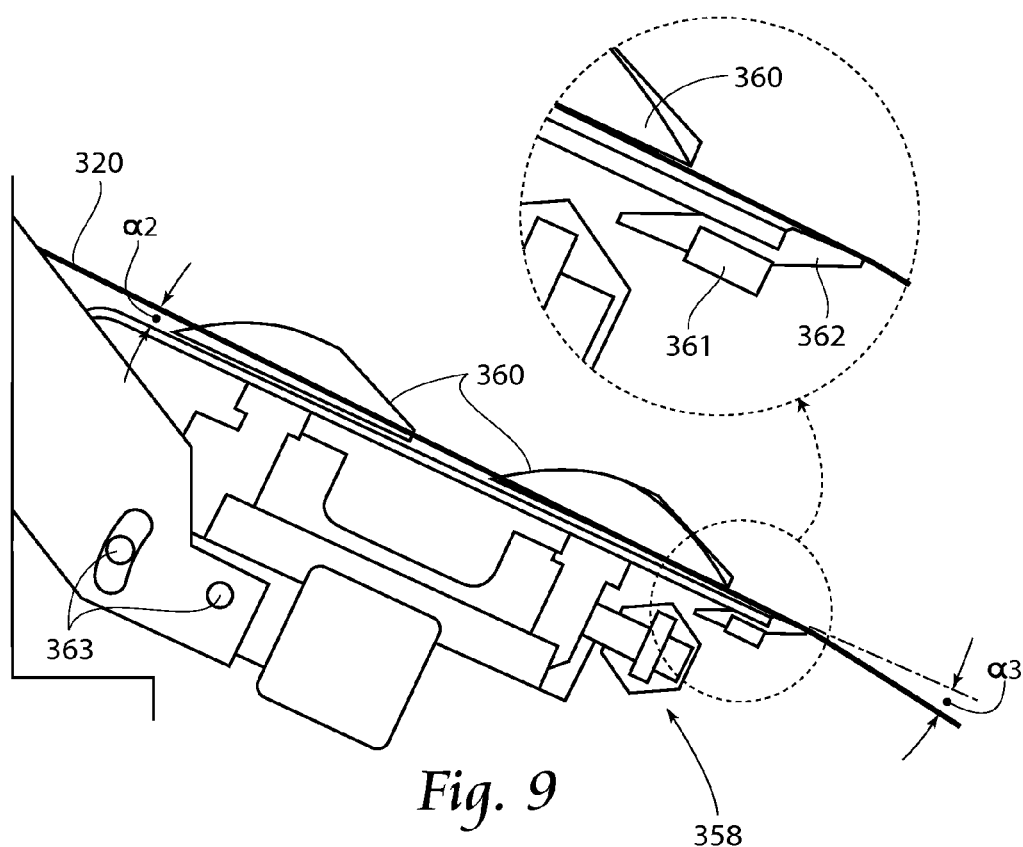
FIG. 9 is a side view, of a portion of automatic cuff defect correction system of the present invention.

Referring now to FIGS. 7-9, an automatic cuff defect correction system 300 is shown. The automatic cuff defect correction system corrects defects that might be present in a fold of non-woven material over strands of elastic intended to be encapsulated within the fold. For instance, the non-woven material may come out of operative engagement with the elastic guide rollers initially used to fold the non-woven, or the elastic material intended to be encapsulated within the folded-over non-woven material may instead not be contained within the folded-over non-woven material as intended.

Referring now to FIG. 7, before entering the cuff folding system 300, the cuff material 310 is first slit into two even width strips and then passes through a web guide (not shown). The operator and drive side cuff webs 310 are driven by cuff infeed drive rolls 305 and fed to cuff infeed idler roller 307. Tape applicator correction unit 323 is operative next to the cuff infeed drive rolls 305.

As the cuff webs 310 pass over the elastic roller guides 340, preferably two adhesive coated strands of elastic 320 are laid down on top of each of the cuff webs 310 just before folding.

Referring again to FIG. 7, the adhesive is applied by glue gun 330, which is adjustable in the upstream and downstream directions by adjusters 332, and by vertical glue gun adjustment system 336, and by the glue gun rotation system 334. In the cross-machine direction, the glue gun adjuster 338 is provided, all to assist proper adhesive application to the elastics 320 being on the infeed.

As best shown on FIG. 8, the cuff fold is created by passing the operator and drive side cuff webs 310 over elastic guide rollers 340. Part of the cuff web 310 extends over the outboard edges of elastic guide rollers 340; it is these portions of cuffs 310 that become folded back on top of the cuff webs 310. The fold is completed as the cuff webs 310 pass over the folding board 380 (FIG. 7) carrying inwardly slidable folding plows 360 on the drive and operator sides with the elastic strands 320 inside the fold of the non-woven material 310. The inwardly slidable folding plows 360 are disengaged (not contacting the cuff webs 310) during run conditions while no defect in the creation of the cuff (elastic 320 contained within folded over cuff web 310) and engaged with the cuff web 310 if a defect is created, to urge the cuff web 310 to return to its proper folded over condition.

Referring again to FIG. 7, the cuff next passes over the cuff outfeed idler roll 308 and chill roll 390 to set the adhesive, and the cuff webs 310 containing the elastics 320 within the folded over portion of the cuff webs 310 are passed on down the line for further processing, including bonding the folded-over non-woven portion of the cuff 310 to the non-folded-over non-woven portion of the cuff 310 to firmly contain the elastics 320 within the fold (not shown), and to finally attach the formed cuff 310 containing the elastics 320 to the appropriate portion of the diaper (not shown).

Still referring to FIG. 7, vision systems 310 are provided on mounts 320, in order to detect defects in the cuff formation process, and to set in motion the appropriate cuff correction process as described below.

1.1 Cuff Correction Systems

The cuff folding system 300 preferably has four cuff correction mode options, described below.

1.1.1 Basic Cuff Correction Mode

The Basic Cuff Correction mode does not utilize the vision system 310, optional tape applicator (not shown), or optional elastic correction rollers 350 (FIG. 8). When a splice between two rolls of incoming non-woven material 310 is detected, the plows 360 will move between the disengaged position (shown in phantom in FIG. 8) to the engaged position (shown in bold in FIG. 8) to allow the splice to pass through the plows 360. Once the splice of non-woven material 310 has passed, the plows will again return to the disengaged position as shown in FIG. 8.

1.1.2 Advanced Cuff Correction Mode

The Advanced Cuff Correction mode incorporates a fold correction sequence and an elastic mistrack sequence.

The fold correction sequence engages the plows 360, the elastic mistrack correction rollers 350, applies tape and the cuff infeed rate is increased to help in the correction of the fold problem. If the system is unable to correct itself after a predetermined period, such as after 5 attempts, a general machine fault can be raised.

The elastic mistrack correction rollers 350 (FIG. 8) are engaged and the cuff infeed rate is increased to help in the correction of an elastic mistrack. If the system is unable to correct itself after a predetermined period, such as after 5 attempts, a general machine fault can be raised.

This mode supports all faults and rejects.

1.1.3 Advanced (Elastic Correction Only) Cuff Correction Mode

The Advanced (Elastic Correction Only) Cuff Correction mode includes everything that comes with the Advanced Cuff Correction mode except for the tape applicator.

Without the tape applicator, the fold correction sequence is different while in this mode. If a fold correction is required, the plows 360 will be engaged (by moving plows 360 slidably between the position shown in dashed lines on FIG. 8, to the position shown in by plows 360 shown by solid lines on FIG. 8). If the fold problem still exists after the plows 360 are engaged, the system can raise an unable to correct cuff fold fault. If the problem no longer exists, the system will return to its normal running state, with the plows 360 returning to their disengaged position (FIG. 8). This mode supports all faults and rejects.

1.1.4 Disabled

All cuff correction system monitoring and corrective action will be disabled regardless of which option is installed.

2. Setup and adjustment 2.1 Cuff System Adjustments 2.1.1 Adhesive adjustments

As shown in FIG. 7, glue gun 330 can be adjusted in the upstream and downstream directions by adjusters 332, and by vertical glue gun adjustment system 336, and by the glue gun rotation system 334. In the cross-machine direction, the glue gun adjuster 338 is provided, all to assist proper adhesive application by positioning and re-positioning the glue gun 330 to the elastics 320 being on the infeed.

When properly positioned, the glue gun heads 330 preferably apply some downward pressure on the elastic strands 320 to deflect them slightly.

The cuff unit cross machine direction adjustment mechanism 352 can be used to adjust the cuff unit in the cross machine direction.

2.2 Elastic Roller Setup

Referring now to FIG. 8 the proper position/relationship between the elastic strands 320, the mistrack corrections rollers 350, elastic guide rollers 340 and plows 360 is shown.

2.3 Idler Roll Adjustments

The proper location for the cuff infeed and outfeed idler rolls are shown in FIGS. 7 and 9.

Referring to FIG. 7, the infeed idler roll 307 is preferably positioned so that the angle between a horizontal reference line tangent to the top of the guide roller 340 and a reference line tangent to the infeed idler roll 307 and guide roller 340 is roughly 15° ($\alpha 1$, FIG. 7).

Still referring to FIG. 7, the outfeed idler roll 308 can be adjusted, preferably so that the angle of the folding board 308 in relation to the cuff web 310 is roughly 1° ($\alpha 3$, FIG. 9). If not, folding board angle adjustment 363, and associated adjustment bolts (not shown) can be used to create a small gap ($\alpha 2$) between the cuff web 310 and the folding board 380 at its entrance.

Referring to FIGS. 7 and 9 still, the outfeed idler roll 308 is preferably positioned so that the angle between a reference line inline with the top of the folding plate 380 and a reference line from the tip of the feather arrest 362 (shown in FIG. 9) and tangent to the outfeed idler roll 308 is 1° ($\alpha 3$, FIG. 9).

A feather arrest 358 consisting of a feather arrest block 362 and nut plate 361 is used to control buildup of process materials which results in product reject or process shutdown. The width of the feather arrest is preferably roughly the same as the folding board or plate 380 and, the feather arrest block 362 mounts to the underside of it by nut plate 361. The feather arrest block 362 has a sloped surface which rises slightly above the plane of the folding plate 380, this causes the cuff web 310 to contact the tip of the feather arrest block 362 (somewhat like a scraper) as it exits the cuff folding assembly. This action minimizes buildup. The feather arrest block 362 preferably has a mirrored shape which allows it to be used a total of four times before needing replacement. The cuff web 310 preferably makes contact with an outboard edges of the feather arrest blocks 362, this allows them to be swapped out between operator and drive side folding boards 380. The mirrored shape of the feather arrest block 362 allows it to be rotated 180° and remounted providing an additional use out of each feather arrest.

3. Operation

3.1 Fold Inspection

If the fold of the non-woven web 310 becomes too narrow or the web width is out of spec on either the drive side or the operator side independently, the fold correction sequence is initiated. The fold correction sequence can be disabled if machine speed is below a predetermined speed, such as 150 ppm, and momentarily when a splice has been detected.

3.2 Fold Correction Sequence

In the fold correction sequence, the plows 360 are engaged, and the elastic mistrack correction rollers 350 are engaged momentarily and the cuff infeed rate is increased to help in the correction of the fold problem. After a brief delay to allow everything to become fully engaged, tape can be applied to the web (not shown) to further assist correcting the fold defect. Should the vision system 370 detect that cuff problems no longer exist during the brief delay, the fold correction sequence is aborted and tape is not applied to the web. Once tape has been applied to the web, the system will wait long enough to evaluate whether the problem still exists, again via vision system 370. If the problem no longer exists, the plows 360 are disengaged, the correction attempts counter is reset, and the cuff infeed 305 is returned to its normal rate. If the problem still exists, the above procedure can be repeated, such as to a preset limit of up to a total of 5 attempts. Then, if desired, if the system is unable to correct itself after 5 attempts, a general machine fault is raised.

3.3 Elastic Inspection

If the inner elastic strand is missing or the fold becomes too wide on either the drive side or the operator side independently, the elastic mistrack correction sequence can be initiated. The elastic mistrack correction sequence is preferably disabled if the system is in the fold correction sequence, if the machine is not at speed set point, or momentarily when a splice has been detected.

3.4 Elastic Mistrack Correction Sequence

In the elastic mistrack correction sequence, the elastic correction rollers 350 are engaged momentarily and the cuff infeed rate is increased to help in the correction of the elastic mistrack. Once the rollers 350 are disengaged, the system will wait long enough to evaluate whether the problem still exists. If the problem no longer exists, an elastic mistrack correction attempts counter is reset and the cuff infeed 305 is returned to its normal rate. If the problem still exists, the above procedure can be repeated a predetermined number of times, such as up to a total of 5 attempts. If the system is unable to correct itself after the predetermined number of attempts, a general machine fault can be raised.

3.5 Process Response

3.5.1 Glue Gun

Intermittent glue is enabled any time speed is above a predetermined speed, such as 100 ppm.

3.5.2 Plows

Plows 360 are engaged when a splice is detected for a set number of products to allow the splice to pass. This action is part of the Advanced Cuff Correction Mode, Advanced (Elastic Correction Only) Cuff Correction Mode, and the Basic Cuff Correction Mode described previously. In addition, the plows 360 engage during the fold correction sequence.

3.5.3 Tape Applicator

Tape can be applied to the web during the fold correction sequence.

3.5.4 Elastic Mistrack Correction Rollers

Elastic mistrack correction rollers 350 are engaged during the elastic mistrack correction sequence. Elastic mistrack correction rollers 350 are engaged at the beginning of each fold correction sequence. Elastic mistrack correction rollers 350 are engaged whenever machine speed is not at set point with two exceptions. First, if the cameras 372 detect a need to run the fold correction sequence, the command to engage the elastic mistrack correction rollers 350 when machine speed is not at set point is disabled. This allows the fold correction sequence to run like normal. Second, the elastic mistrack correction rollers 350 will not engage during ramp-down even though the machine speed is not at set point during this time.

3.5.5 Reduced Tension (Increased Infeed Rate)

Under four different scenarios, the cuff infeed rate is increased by a predetermined amount, such as 0.75 mm, to reduce tension. First, if the splicer sequence activates at the unwind of the cuff webs 310, the cuff infeed rate is increased until the splice has passed the folding boards 380. Second, whenever machine speed is not at set point, the cuff infeed rate is increased to help maintain the cuff fold. Third, if the system ever enters the fold correction sequence, the cuff infeed rate is increased to help in the correction of the fold. Last, if the system ever enters the elastic mistrack correction sequence, the cuff infeed rate is increased to help in the correction of the elastic mistrack.

3.5.6 Ramp-Up Notes

The elastic mistrack correction rollers 350 are engaged during ramp-up because the machine speed is not at set point. The fold correction sequence will take place if the need arises once machine speed equals or exceeds a predetermined amount, such as 150 ppm. If a fold correction sequence occurs, the command to enable the elastic mistrack correction rollers when the machine speed is not at set point is momentarily disabled. The elastic mistrack correction sequence is disabled during ramp-up, and the cuff infeed rate is increased to help maintain the cuff fold.

3.5.7 Ramp-Down Notes

The fold correction sequence will take place during ramp-down if the need arises and the machine speed still exceeds a predetermined amount, such 150 ppm. The elastic mistrack correction sequence is disabled during ramp-down.

3.5.8 Splice Notes

When a splice in one of the incoming cuff webs 310 is detected, the plows 360 engage and the fold correction sequence and the elastic mistrack correction sequence are disabled. The plows 360 remain engaged for a product count long enough to allow the splice to pass through the plows and pass the vision system. Once the product count has been met, the plows 360 will disengage and the fold correction sequence and the elastic mistrack correction system will be enabled. When the splicer sequence activates at the unwind, the cuff infeed rate is increased until the splice has passed the folding boards.

3.6 Faults

The Advanced Cuff Correction System and the Advanced (Elastic Correction Only) Cuff Correction System can raise 4 different general machine faults. If the drive side camera 372 OK status signal is not present, a cuff vision system drive side camera fault is raised. If the operator side camera 372 OK status signal is not present, a cuff vision system operator side camera fault is raised. If the fold correction sequence fails to fix a detected problem in a predetermined number of attempts, it will raise an unable to correct cuff fold fault. If the elastic mistrack correction sequence fails to fix a detected problem in a predetermined number of attempts, it will raise an unable to correct cuff elastic/glue fault. Glue is noted in this fault description because a lack of glue on the elastic strands 320 will cause the camera 372 to be unable to detect it.

3.7 Rejects

Rejects are caused any time the system enters the fold correction sequence or the elastic mistrack correction sequence until problems are no longer detected. Due to the nature of the vision system 372, rejects from the cuff vision system have a speed dependency and need to have the offsets and quantities set at the desired running speed. There are 8 different reject reasons caused by the Advanced Cuff Correction System and the Advanced (Elastic Correction Only) Cuff Correction System. These are drive side web width out of spec, drive side fold too narrow, drive side fold too wide, drive side inner elastic strand missing, operator side web width out of spec, operator side fold too narrow, operator side fold too wide, and operator side inner elastic strand missing.

4. Troubleshooting 4.1 Cuff Problems Possible Causes:

No glue coming from glue nozzle 330
Plugged up glue nozzle 330
Slitting cuff web 310 unevenly between drive side and operator side
Fold over width set incorrectly on the drive side or operator side
Buildup on the plows 360 are not allowing for fold correction
Buildup on the folding boards 380 is effecting fold width
Buildup on the feather arrest 362 is effecting fold width
Glue buildup in the elastic guide rollers 340
Glue buildup on the elastic mistrack correction roller 350
Camera lens 372 may need to be cleaned
Camera light may need to be cleaned
Web guide photoeyes may need to be cleaned
An elastic strand 320 is broken
Both elastic strands 320 in the same glue nozzle 330 lane
Chill roll 390 is not functioning
Cuff nip rolls (not shown) are either not engaged or covered in buildup
Tape roll (not shown) is empty or web is broken
Folding plows 360 adjusted incorrectly for fixing a fold problem
Folding boards 380 are either tipped up too much or too little
Cuff raw material 310 may be too wide or too narrow
Cuff draws set incorrectly
Glue nozzles 330, elastic guide rollers 340, elastic mistrack correction rollers 350, and folding plows 360 may no longer be setup according to the cuff setup document
Camera light may not be functioning
Cameras 372 lost communication to the PLC
Camera 372 is no longer centered over the folded cuff
Either of the two camera cables are disconnected
Either of the two camera cables are malfunctioning
Camera inspection is not running
Camera lens is out of focus
Camera lens aperture setting not correct
Camera lens is loose
Camera needs to be recalibrated
Infrared filter is not screwed onto the lens 4.2 Corrective Actions If cuff problems start occurring, a thorough cleaning of all the cuff folding pieces can help
Visual verification that there is a good glue pattern on each elastic strand 320
Verify that the cuff 310 is being slit evenly between the operator and drive side and adjust the web-guide photoeyes if needed
Verify that each cuff 310 is being folded over the correct amount and adjust the web-guide photoeyes if needed
If problems continue to occur, the vision system 372 may need to be checked for functionality
Verify the cameras 372 and light are operational
Verify the camera 372 is communicating with the PLC
To verify proper functionality of the vision system by viewing images from the camera 372, connect to the camera using vision software (not shown)
Take care not to modify the camera inspection program while connected to the camera 372
Verify the cuff inspection is running The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A method for correcting defects in a running web comprising:
creating a running fold having a cross-direction fold width in an initial condition along a machine direction of a running web supplied at a feed rate;
monitoring said running fold for a predetermined change in cross-direction fold width of said fold width from said initial condition;
upon detection of said predetermined change in said cross-direction fold width of said fold width from said initial condition, initiating a correction sequence to restore said running fold to said initial condition; wherein said correction sequence further comprises the steps of:
engaging a mistrack correction roller against the running web; and
disengaging said mistrack correction roller from the running web.

2. A method according to claim 1, wherein, if said fold width is too narrow, said correction sequence further comprises the step of urging a folding plow into engagement with said running web.

3. A method according to claim 1, further comprising a step of increasing said feed rate after engaging said mistrack correction roller and then decreasing said feed rate after the step of increasing said feed rate.

* * * * *